(12) United States Patent
Hartman

(10) Patent No.: US 10,077,239 B2
(45) Date of Patent: Sep. 18, 2018

(54) CRYSTALLINE FORMS OF A HEPATITIS B ANTIVIRAL AGENT

(71) Applicant: NOVIRA THERAPEUTICS, INC, Doylestown, PA (US)

(72) Inventor: George D. Hartman, Lansdale, PA (US)

(73) Assignee: NOVIRA THERAPEUTICS, INC., Doylestown, PA (US)

(*) Notice: Subject to any disclaimer, the term of this patent is extended or adjusted under 35 U.S.C. 154(b) by 42 days.

(21) Appl. No.: 15/280,321

(22) Filed: Sep. 29, 2016

(65) Prior Publication Data

US 2017/0114018 A1   Apr. 27, 2017

Related U.S. Application Data

(60) Provisional application No. 62/234,124, filed on Sep. 29, 2015.

(51) Int. Cl.
  *C07D 211/96* (2006.01)

(52) U.S. Cl.
  CPC ........ *C07D 211/96* (2013.01); *C07B 2200/13* (2013.01)

(58) Field of Classification Search
  CPC .................................................. C07D 211/96
  See application file for complete search history.

(56) References Cited

U.S. PATENT DOCUMENTS

| | | | |
|---|---|---|---|
| 3,843,662 A | 10/1974 | Holland | |
| 4,569,940 A | 2/1986 | Watts | |
| 4,962,101 A | 10/1990 | Dininno et al. | |
| 5,272,167 A | 12/1993 | Girijavallabhan et al. | |
| 5,308,826 A | 5/1994 | Chin et al. | |
| 5,314,880 A | 5/1994 | Whittaker et al. | |
| 5,585,327 A | 12/1996 | Chin et al. | |
| 5,607,929 A | 3/1997 | Nicol | |
| 5,708,034 A | 1/1998 | Kleemann et al. | |
| 5,723,411 A | 3/1998 | Stevenson | |
| 5,795,907 A | 8/1998 | Kalindjian et al. | |
| 5,912,260 A | 6/1999 | Kalindjian et al. | |
| 5,919,970 A | 7/1999 | Song et al. | |
| 5,939,423 A | 8/1999 | Karlin | |
| 6,025,367 A | 2/2000 | Forbes et al. | |
| 6,265,408 B1 | 7/2001 | Forbes et al. | |
| 6,476,025 B1 | 11/2002 | Flockerzi et al. | |
| 6,650,463 B2 | 11/2003 | Obikawa et al. | |
| 6,668,527 B2 | 12/2003 | Chupak et al. | |
| 6,780,389 B2 | 8/2004 | Karl et al. | |
| 7,115,595 B2 | 10/2006 | Sunagawa et al. | |
| 7,186,735 B2 | 3/2007 | Strobel et al. | |
| 7,338,956 B2 | 3/2008 | Strobel et al. | |
| 7,368,457 B2 | 5/2008 | Josien et al. | |
| 7,384,967 B2 | 6/2008 | Polisetti et al. | |
| 7,576,688 B2 | 1/2009 | Suzuki et al. | |
| 7,541,373 B2 | 6/2009 | Polisetti et al. | |
| 7,544,700 B2 | 6/2009 | Halazy et al. | |
| 7,595,322 B2 | 9/2009 | Morgan et al. | |
| 7,608,723 B2 | 10/2009 | Boyce et al. | |
| 7,750,158 B2 | 7/2010 | Shankar et al. | |
| 7,786,104 B2 | 8/2010 | Dubois et al. | |
| 7,790,726 B2 | 9/2010 | Zhang et al. | |
| 7,838,525 B2 | 11/2010 | Jones et al. | |
| 7,888,373 B2 | 2/2011 | Morgan et al. | |
| 7,994,168 B2 | 8/2011 | Lennig et al. | |
| 8,071,779 B2 | 12/2011 | Richards et al. | |
| 8,084,457 B2 | 12/2011 | Choidas et al. | |
| 8,097,728 B2 | 1/2012 | Gu et al. | |
| 8,101,620 B2 | 1/2012 | Morgan et al. | |
| 8,153,650 B2 | 4/2012 | Dubois et al. | |
| 8,153,803 B2 | 4/2012 | Kazantsev et al. | |
| 8,207,195 B2 | 6/2012 | Navratil et al. | |
| 8,227,489 B2 | 7/2012 | Dubois et al. | |
| 8,273,754 B2 | 9/2012 | Hill et al. | |
| 8,299,096 B2 | 10/2012 | Navratil et al. | |
| 8,299,114 B2 | 10/2012 | Dubois et al. | |
| 8,354,425 B2 | 1/2013 | Dubois et al. | |
| 8,394,820 B2 | 3/2013 | Dubois et al. | |
| 8,399,491 B2 | 3/2013 | Dubois et al. | |
| 8,404,747 B2 | 3/2013 | Kazantsev et al. | |
| 8,410,147 B2 | 4/2013 | Peterson et al. | |
| 8,536,168 B2 | 9/2013 | Dai et al. | |
| 8,609,668 B2 | 12/2013 | Cuconati et al. | |
| 8,629,274 B2 | 1/2014 | Hartman et al. | |
| 8,808,702 B2 | 8/2014 | Reddy et al. | |
| 8,889,716 B2 | 11/2014 | Prime et al. | |
| 8,993,771 B2 | 3/2015 | Hartman et al. | |

(Continued)

FOREIGN PATENT DOCUMENTS

| | | |
|---|---|---|
| CA | 2950807 A1 | 12/2015 |
| CN | 102093320 A | 6/2011 |
| EP | 0 232 067 A2 | 8/1987 |
| EP | 0 742 200 B1 | 7/1999 |
| EP | 2 280 001 A1 | 2/2011 |
| JP | S62-142164 A | 6/1987 |
| JP | 2008-525406 A | 7/2008 |
| JP | 2008-179621 A | 8/2008 |
| JP | 2010-535172 A | 11/2010 |
| WO | 1984/003281 A1 | 8/1984 |
| WO | 1992/007835 A1 | 5/1992 |
| WO | 1998/023285 A1 | 6/1998 |
| WO | 1999/009022 A1 | 2/1999 |
| WO | 1999/038845 A1 | 8/1999 |
| WO | 1999/048492 A1 | 9/1999 |

(Continued)

OTHER PUBLICATIONS

The Merck Index (2013) "Zidovudine," An Encyclopedia of Chemicals, Drugs and Biologicals. 14th Ed. p. 1885.

(Continued)

*Primary Examiner* — Noble E Jarrell
*Assistant Examiner* — John S Kenyon
(74) *Attorney, Agent, or Firm* — Brian C. Trinque; Benjamin Vaughan; Lathrop Gage LLP

(57) ABSTRACT

This disclosure provides crystalline forms of a hepatitis B antiviral agent, and methods of making and using these forms.

11 Claims, 20 Drawing Sheets

(56) References Cited

U.S. PATENT DOCUMENTS

| | | |
|---|---|---|
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil Van Niel et al. |
| RE45,670 E | 9/2015 | Polisetti et al. |
| 9,169,212 B2 | 10/2015 | Hartman et al. |
| 9,181,288 B2 | 11/2015 | Hartman et al. |
| 9,205,079 B2 | 12/2015 | Hartman et al. |
| 9,339,510 B2 | 5/2016 | Hartman et al. |
| 9,400,280 B2 | 7/2016 | Hartman |
| 9,458,176 B2 | 10/2016 | Takaishi et al. |
| 9,505,722 B2 | 11/2016 | Hartman et al. |
| 2002/0049236 A1 | 4/2002 | Chupak et al. |
| 2004/0039009 A1 | 2/2004 | Jagtap et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0325960 A1 | 1/2009 | Fulcher et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2010/0008968 A1 | 1/2010 | Vittitow et al. |
| 2010/0016310 A1 | 1/2010 | Ingraham |
| 2010/0022517 A1 | 1/2010 | Richards et al. |
| 2010/0204210 A1 | 8/2010 | Sorensen et al. |
| 2011/0009622 A1 | 1/2011 | Jitsuoka et al. |
| 2011/0064695 A1 | 3/2011 | Qiu et al. |
| 2011/0064696 A1 | 3/2011 | Or et al. |
| 2011/0184019 A1 | 6/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Vittitow et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 9/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman et al. |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0259324 A1 | 9/2015 | Hartman et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0115125 A1 | 4/2016 | Vandyck et al. |
| 2016/0158214 A1 | 6/2016 | Hartman |
| 2016/0272599 A1 | 9/2016 | Hartman et al. |
| 2017/0015629 A1 | 1/2017 | Hartman et al. |

FOREIGN PATENT DOCUMENTS

| | | | |
|---|---|---|---|
| WO | 1999/065906 A1 | 12/1999 | |
| WO | 2001/005390 A2 | 1/2001 | |
| WO | 2001/019788 A2 | 3/2001 | |
| WO | 2001/051487 A1 | 7/2001 | |
| WO | 2001/055121 A1 | 8/2001 | |
| WO | 2001/085694 A2 | 11/2001 | |
| WO | 2002/051410 A2 | 7/2002 | |
| WO | 2002/064618 A2 | 8/2002 | |
| WO | 2003/007955 A2 | 1/2003 | |
| WO | 2003/044016 A1 | 5/2003 | |
| WO | 2003/101961 A1 | 12/2003 | |
| WO | 2004/010943 A2 | 2/2004 | |
| WO | 2004/011427 A2 | 2/2004 | |
| WO | 2004/022060 A2 | 3/2004 | |
| WO | 2004/058709 A1 | 7/2004 | |
| WO | 2004/086865 A1 | 11/2004 | |
| WO | 2004/099192 A2 | 11/2004 | |
| WO | 2004/100947 A2 | 11/2004 | |
| WO | 2005/016922 A2 | 2/2005 | |
| WO | 2005/044797 A1 | 5/2005 | |
| WO | 2005/087217 A1 | 9/2005 | |
| WO | 2005/105785 A2 | 11/2005 | |
| WO | 2005/115374 A1 | 12/2005 | |
| WO | 2006/002133 A1 | 1/2006 | |
| WO | 2006/024834 A1 | 3/2006 | |
| WO | 2006/053109 A1 | 5/2006 | |
| WO | 2006/067445 A2 | 6/2006 | |
| WO | 2006/067446 A1 | 6/2006 | |
| WO | 2006/123257 A2 | 11/2006 | |
| WO | 2006/128129 A2 | 11/2006 | |
| WO | 2006/128172 A2 | 11/2006 | |
| WO | 2007/031791 A1 | 3/2007 | |
| WO | 2008/011476 A2 | 1/2008 | |
| WO | 2008/022171 A1 | 2/2008 | |
| WO | 2008/093614 A1 | 8/2008 | |
| WO | 2008/137794 A1 | 11/2008 | |
| WO | 2008/154819 A1 | 12/2008 | |
| WO | 2009/016088 A1 | 2/2009 | |
| WO | 2009/062402 A1 | 5/2009 | |
| WO | 2009/086303 A2 | 7/2009 | |
| WO | 2009/131065 A1 | 10/2009 | |
| WO | 2009/146013 A1 | 12/2009 | |
| WO | 2010/018113 A2 | 2/2010 | |
| WO | 2010/043592 A1 | 4/2010 | |
| WO | 2010/088000 A2 | 8/2010 | |
| WO | 2010/123139 A1 | 10/2010 | |
| WO | 2011/002635 A1 | 1/2011 | |
| WO | 2011/035143 A2 | 3/2011 | |
| WO | 2011/088015 A1 | 7/2011 | |
| WO | 2011/088561 A1 | 7/2011 | |
| WO | 2011/109237 A2 | 9/2011 | |
| WO | 2011/112191 A1 | 9/2011 | |
| WO | 2011/123609 A1 | 10/2011 | |
| WO | 2011/140324 A1 | 11/2011 | |
| WO | 2011/155898 A1 | 12/2011 | |
| WO | 2012/016133 A2 | 2/2012 | |
| WO | 2012/018635 A2 | 2/2012 | |
| WO | 2012/033956 A1 | 3/2012 | |
| WO | 2012/049277 A1 | 4/2012 | |
| WO | 2012/075235 A1 | 6/2012 | |
| WO | 2012/080050 A1 | 6/2012 | |
| WO | 2012/117216 A1 | 9/2012 | |
| WO | 2012/136834 A1 | 10/2012 | |
| WO | 2013/006394 A1 | 1/2013 | |
| WO | 2013/096744 A1 | 6/2013 | |
| WO | WO 2013096744 A1 * | 6/2013 | ........... A61K 31/407 |
| WO | 2013/102655 A1 | 7/2013 | |
| WO | 2013/130703 A2 | 9/2013 | |
| WO | 2013/181584 A2 | 12/2013 | |
| WO | 2013/184757 A1 | 12/2013 | |
| WO | 2014/033167 A1 | 3/2014 | |
| WO | 2014/033170 A1 | 3/2014 | |
| WO | 2014/033176 A1 | 3/2014 | |
| WO | 2014/037480 A1 | 3/2014 | |
| WO | 2014/106019 A2 | 7/2014 | |
| WO | 2014/131847 A1 | 9/2014 | |
| WO | 2014/151958 A1 | 9/2014 | |
| WO | 2014/161888 A1 | 10/2014 | |
| WO | 2014/184350 A1 | 11/2014 | |
| WO | 2014/184365 A1 | 11/2014 | |

(56) References Cited

FOREIGN PATENT DOCUMENTS

| | | |
|---|---|---|
| WO | 2014/191301 A1 | 12/2014 |
| WO | 2014/191726 A1 | 12/2014 |
| WO | 2014/198880 A1 | 12/2014 |
| WO | 2015/011281 A1 | 1/2015 |
| WO | 2015/055764 A1 | 4/2015 |
| WO | 2015/057945 A1 | 4/2015 |
| WO | 2015/059212 A1 | 4/2015 |
| WO | 2015/073774 A1 | 5/2015 |
| WO | 2015/109130 A1 | 7/2015 |
| WO | 2015/116923 A1 | 8/2015 |
| WO | 2015/138895 A1 | 9/2015 |
| WO | 2015/144093 A1 | 10/2015 |
| WO | 2015/180631 A1 | 12/2015 |
| WO | 2016/089990 A1 | 6/2016 |
| WO | 2016/109663 A2 | 7/2016 |
| WO | 2016/109684 A2 | 7/2016 |
| WO | 2016/109689 A2 | 7/2016 |
| WO | 2016/113273 A1 | 7/2016 |
| WO | 2016/149581 A1 | 9/2016 |
| WO | 2016/161268 A1 | 10/2016 |
| WO | 2016/168619 A1 | 10/2016 |
| WO | 2016/183266 A1 | 11/2016 |
| WO | WO-2017181141 A2 * | 10/2017 ............. A61K 31/40 |

OTHER PUBLICATIONS

Thompson et al. (2007) "Toll-like receptors, RIG-I-like RNA helicases and the antiviral innate immune response," Immunology and Cell Biology. 85:435-445.
Weber et al. (2002) "Inhibition of human hepatitis B virus (HBV) by a novel non-nucleosidic compound in a transgenic mouse model," Antiviral Res. 54:69-78.
West (1984) Solid State Chemistry and its Applications. John Wiley & Sons. pp. 33-36.
Yarmolchuk (2011) "Synthesis of β-fluoro-β-proline," Tetrahedron Letters. 51(12):1300-1302.
Zhang et al. (2005) "A Potent Small Molecule Inhibits Polyglutamine Aggregation in Huntington's Disease Neurons and Suppresses Neurodegeneration in vivo," Proc. Natl. Acad. Sci. USA. 102(3):892-897.
U.S. Appl. No. 13/723,869, filed Dec. 21, 2012, 2013/0251673, Sep. 26, 2013, U.S. Pat. No. 8,629,274, Jan. 14, 2014, George D. Hartman.
U.S. Appl. No. 14/100,219, filed Dec. 9, 2013, 2014/0179665, Jun. 26, 2014, U.S. Pat. No. 9,061,008, Jun. 23, 2015, George D. Hartman.
U.S. Appl. No. 14/134,113, filed Dec. 19, 2013, 2014/0178337, Jun. 26, 2014, U.S. Pat. No. 9,066,932, Jun. 30, 2015, George D. Hartman.
U.S. Appl. No. 14/517,606 filed Oct. 17, 2014, 2015/0152073, Jun. 4, 2015, George D. Hartman.
U.S. Appl. No. 14/728,126, filed Jun. 2, 2015, 2015/0259324, Sep. 17, 2015, George D. Hartman.
U.S. Appl. No. 14/206,496, filed Mar. 12 2014, 2014/0275167, Sep. 18, 2014, U.S. Pat. No. 8,993,771, Mar. 31, 2015, George D. Hartman.
U.S. Appl. No. 14/642,393, filed Mar. 9, 2015, 2015/0174115, Jun. 25, 2015, U.S. Pat. No. 9,205,079, Dec. 8, 2015, George D. Hartman.
U.S. Appl. No. 14/931,173, filed Nov. 3, 2015, 2016/0158214, Jun. 9, 2016, George D. Hartman.
U.S. Appl. No. 14/511,964, filed Oct. 10, 2014, 2015/0197493, Jul. 16, 2015, U.S. Pat. No. 9,169,212, Oct. 27, 2015, George D. Hartman.
U.S. Appl. No. 14/694,147, filed Apr. 23, 2015, 2015/0225355, Aug. 13, 2015, U.S. Pat. No. 9,505,722, Nov. 29, 2016, George D. Hartman.
U.S. Appl. No. 14/597,814, filed Jan. 15, 2015, 2015/0197533, Jul. 16, 2015, U.S. Pat. No. 9,181,288, Nov. 10, 2015, George D. Hartman.
U.S. Appl. No. 14/856,761, filed Sep. 17, 2015, 2016/0000812, Jan. 7, 2016, U.S. Pat. No. 9,339,510, May 17, 2016, George D. Hartman.
U.S. Appl. No. 15/277,421, filed Sep. 27, 2016, 2017/0015629, Jan. 19, 2017, George D. Hartman.
U.S. Appl. No. 14/670,001, filed Mar. 26, 2015, 2015/0274652, Oct. 1, 2015, U.S. Pat. No. 9,400,280, Jul. 26, 2016, George D. Hartman.
U.S. Appl. No. 14/615,292, filed Feb. 5, 2015, 2015/0216938, Aug. 6, 2015, George D. Hartman.
U.S. Appl. No. 15/284,807, filed Oct. 4, 2016, George D. Hartman.
U.S. Appl. No. 15/073,965, filed Mar. 18, 2016, 2016/0272599, Sep. 22, 2016, George D. Hartman.
[Online] Registry via SciFinfer, Feb. 13, 2017, RN 1208400-27-4.
Brahmania (Jan. 13, 2016) "New therapeutic agents for chronic hepatitis B," Lancet Infect. Dis. 16(2):e10-e21.
Brezillon et al. (2011) "Antiviral activity of Bay 41-4109 on hepatitis B virus in humanized Alb-uPA/SCID mice," PLoS One. 6:e25096. pp. 1-6.
Chang et al. (2007) "NMR-spectroscopy-based metabonomic approach to the analysis of Bay41-4109, a novel anti-HBV compound, induced hepatotoxicity in rats," Tox. Letters. 173:161-167.
Cho et al. (Dec. 25, 2013) "2-amino-N-(2,6-dichloropyridin-3-yl)acetamide derivatives as a novel class of HBV capsid assembly inhibitor," Viral Hep. 21:843-852.
Cowie et al. (Jun. 11, 2013) "Mortality due to viral hepatitis in the Global Burden of Disease Study 2010: new evidence of an urgent global public health priority demanding action," Antivir. Ther. 18:953-954.
Delaney et al. (2002) "Phenylpropenamide derivatives AT-61 and AT-130 inhibit replication of wild-type and lamivudine-resistant strains of hepatitis B virus in vitro," Antimicrob. Agents Chemother. 46:3057-3060.
Deres et al. (2003) "Inhibition of hepatitis B virus replication by drug-induced depletion of nucleocapsids," Science. 299:893-896.
Gane (2014) "Phase 1a Saftey and Pharmacokinetics of NVR 3-778, a Potential First-in-Class HBV Core Inhibitor," In; The Abstracts of the Liver Meeting 2014 (AASLD). Boston, MA. Abstract LB-19.
Guo (2011) "HBc binds to the CpG islands of HBV cccDNA and promotes an epigenetic permissive state," Epigenetics. 6:720-726.
Huang et al. (Oct. 2016) "Blockage of HBV Virus Replication and Inhibition of cccDNA Establishment by Core Protein Allosteric Modifiers (CpAMs)," In; The Abstracts of the Liver Meeting 2016 (AASLD). Boston, MA. po. 937A-938A. Abstract 1897.
Katen et al. (Jul. 18, 2013) "Assembly-directed antivirals differentially bind quasiequivalent pockets to modify hepatitis B virus capsid tertiary and quaternary structure," Structure. 21(8)1406-1416.
Klumpp et al. (2015) "O115: High antiviral activity of the HBV core inhibitor NVR 3-778 in the humanized uPA/SCID mouse model," J. Hepatol. 62:S250.
Klumpp et al. (Nov. 23, 2015) "High-resolution crystal structure of a hepatitis B virus replication inhibitor bound to the viral core protein," Proc. Natl. Acad. Sci. 112:15196-15201.
Lam et al. (Oct. 2015) "Inhibition of Hepatitis B Virus Replication by the HBV Core Inhibitor NVR 3-778," In; The Abstracts of the Liver Meeting 2015 (AASLD). San Francisco, CA. p. 223A. Abstract 33.
Lam et al. (Oct. 2016) "HBV Core Assembly Modulators Block Antigen Production when Present during Infection, but not during Persistent Infection," In; The Abstracts of the Liver Meeting 2016 (AASLD). Boston, MA p. 913A Abstract 1850.
Lam et al. (Sep. 2016) "Serum HBV RNA as a Pharmacodynamic (PD) Marker of HBV Treatment Response to Core Assembly Modulator NVR 3-778 and Pegylated-Interferon Alpha," Poster Presented In; The AASLD/EASL HBV Treatment Endpoints Workshop. Alexandria, VA. Sep. 8-9, 2016. Poster No. 3774.
Lucifora et al. (Feb. 20, 2014) "Specific and nonhepatotoxic degradation of nuclear hepatitis B virus cccDNA," Science. 343:1221-1228.
Manzoor et al. (Nov. 28, 2015) "Hepatitis B virus therapy: What's the future holding for us?" World J Gastro. 21:12558-12575.

(56) References Cited

OTHER PUBLICATIONS

Qiu et al. (Aug. 10, 2016) "Design and Synthesis of Orally Bioavailable 4-Methyl Heteroaryldihydropyrimidine Based Hepatitis B Virus (HBV) Capsid Inhibitors," J. Med. Chem. 59:7651-7666.
Stray et al. (2005) "A heteroaryldihydropyrimidine activates and can misdirect hepatitis B virus capsid assembly," Proc. Natl. Acad. Sci. USA. 102:8138-8143.
Stray et al. (2006) "BAY 41-4109 has multiple effects on Hepatitis B virus capsid assembly," J. Mol. Recognit. 19:542-548.
Tan et al. (Jan. 2, 2013) "Genetically altering the thermodynamics and kinetics of hepatitis B virus capsid assembly has profound effects on virus replication in cell culture," J. Vir. 87:3208-3216.
Wang et al. (Jun. 6, 2012) "In vitro inhibition of HBV replication by a novel compound, GLS4, and its efficacy against adefovir-dipivoxil-resistant HBV mutations," Antiviral therapy 17:793-803.
Wang et al. (May 28, 2016) "Serum hepatitis B virus RNA is encapsidated pregenome RNA that may be associated with persistence of viral infection and rebound," J. Hepatol. 65:700-710.
Wu et al. (Aug. 19, 2013) "Preclinical characterization of GLS4, an inhibitor of hepatitis B virus core particle assembly," Antimicrob. Agents Chemother. 57:5344-5354.
Yang et al. (2016) "Effect of a hepatitis B virus inhibitor, NZ-4, on capsid formation," Antiviral Res. 125:25-33.
Yang et al. (Feb. 3, 2014) "Isothiafiudine, a novel non-nucleoside compound, inhibits hepatitis B virus replication through blocking pregenomic RNA encapsidation," Acta Pharmacol. Sin. 35:410-418.
Yofaratnam et al. (Oct. 2016) "Safety, Tolerability and Pharmacokinetics of JNJ-56136379, a Novel HBV Caspid Assembly Modulator, in Healthy Subjects," In; The Abstracts of the Liver Meeting 2016 (AASLD). Boston, MA. po. 930A-931A. Abstract 1881.
Yuen et al. (Apr. 2016) "NVR 3-778, a first-in-class HBV CORE inhibitor, alone and incombination with Peg-interferon (PEGFIN), in treatment naive HBeAg-Positive patients: early reductions in HBV DNA and HBeAg," In; The Abstracts of the International Liver Congress (EASL). pp. S210-S211. Abstract LB-06.
Yuen et al. (Oct. 2015) "Phase 1b Efficacy and Safety of NVR 3-778, a First-In-Class HBV Core Inhibitor, in HBeAg-Positive Patients with Chronic HBV Infection," In; The Abstracts of the Liver Meeting 2015 (AASLD). San Francisco, CA. pp. 1385A-1386A Abstract LB-10.
Zlotnick et al. (Jun. 27, 2015) "Core protein: a pleiotropic keystone in the HBV lifecycle," Antiviral Research. 121:82-93.
Zoulim et al. (Jun. 15, 2016) "Current treatments for chronic hepatitis B virus infections," Curr. Opin. Virol. 18:109-116.
[Online] CAS (STN), 148:183450, RN 296790-26-6.
[Online] Registry via STN, May 6, 2011, RN 1291044-81-9.
[Online] Registry via STN, Oct. 7, 2008, RN 1057788-44-9.
[Online] Registry via STN, Oct. 7, 2008, RN 1057871-39-2.
[Online] Registry via STN, Aug. 15, 2011, RN 1317923-24-2.
[Online] Registry via STN, Aug. 15, 2011, RN 1318022-74-0.
[Online] Registry via STN, May 18, 2011, RN 1296380-95-4.
[Online] Registry via STN, Oct. 18, 2000, RN 296894-70-7.
[Online] Registry via STN, Sep. 20, 2013, RN 1452780-00-5.
Bennes et al. (2001) "Recognition-induced control and acceleration of a pyrrole Diels-Alder reaction," Tetrahedron Letters. 42(12):2377-2380.
Berke et al. (Oct. 2016) "Caspid assembly modulator JNJ-56136379 prevents de novo infection of primary human hepatocytes with hepatitis B virus," In; The Abstracts of the Liver Meeting 2016 (AASLD). Boston, MA. p. 124A. Abstract 234.
Cai et al. (Aug. 2012) "Identification of Disubstituted Sulfonamide Compounds as specific Inhibitors of Hepatitis B Virus Covalently Closed Circular DNA Formation," Antimicrobial Agents and Chemotherapy. 56(8):4277-4288.
Campagna et al. (Apr. 10, 2013) "Sulfonamoylbenzamides Derivatives Inhibit the Assembly of Hepatitis B virus in Nucleocapsids," J. Virol. 87(12):6931-6942.

Duan et al. (2009) "2-Phenylquinazolin-4(3H)-one, a class of potent PDES inhibitors with high selectivity versus PDE6," Bioorganic and Medicinal Chemistry. 19(10):2777-2779.
El-Sayed (1998) "A Comparative Study of the Reactions of Thiophene-2-Carboxanilides and Related Compounds," Chemistry of Heterocyclic Compounds. 34(7):796-801.
El-Sharief et al. (1987) "Synthesis of different types of chlorinated sulfonamides with expected insecticidal and bactericidal activities," Proceedings of the Indian National Science Academy, Part A: Physical Sciences. 53(1):179-188.
Ermann et al. (2008) "Arylsulfonamide CB2 receptor agonists: SAR and optimization of CB2 selectivity," Bioorganic & Medicinal Chemistry Letters. 18(5):1725-1729.
Extended European Search Report corresponding to European Patent Application No. 12182076, dated Apr. 19, 2013.
Extended European Search Report corresponding to European Patent Application No. 13157232, dated Apr. 5, 2013.
Extended European Search Report corresponding to European Patent Application No. 13162131, dated Sep. 11, 2013.
Extended European Search Report corresponding to European Patent Application No. 13168291, dated Jun. 20, 2013.
Extended European Search Report corresponding to European Patent Application No. 13168295, dated Oct. 7, 2013.
Extended European Search Report corresponding to European Patent Application No. 13169574, dated Aug. 19, 2013.
Geies (1991) "Synthesis of Some Thiazolo-[3, 2=A]Pyrimidines," Phosphorous, Sulfur and Silicon and the Related Elements. 56(1-4):87-93.
Hogan (2009) "Aqueous Process Chemistry: The Preparation of Aryl Sulfonyl Chlorides," Organic Process Research and Development. 13(5):875-879.
International Search Report with Written Opinion corresponding to International Patent Application No. PCT/EP2013/067821, dated Nov. 28, 2013.
International Search Report with Written Opinion corresponding to International Patent Application No. PCT/EP2013/067829, dated Jan. 10, 2014.
International Search Report with Written Opinion corresponding to International Patent Application No. PCT/EP2014/053858, dated May 28, 2014.
International Search Report with Written Opinion corresponding to International Patent Application No. PCT/EP2014/056601, dated Jun. 13, 2014.
International Search Report with Written Opinion corresponding to International Patent Application No. PCT/EP2014/060102, dated Jul. 7, 2014.
International Search Report with Written Opinion corresponding to International Patent Application No. PCT/EP2014/060132, dated Jun. 16, 2014.
International Search Report with Written Opinion corresponding to International Patent Application No. PCT/US2012/071195, dated Dec. 21, 2012.
International Search Report with Written Opinion corresponding to International Patent Application No. PCT/US2014/024509, dated Oct. 22, 2014.
International Search Report with Written Opinion corresponding to International Patent Application No. PCT/US2015/011663, dated Apr. 29, 2015.
International Search Report with Written Opinion corresponding to International Patent Application No. PCT/US2015/014663, dated Apr. 6, 2015.
International Search Report with Written Opinion corresponding to International Patent Application No. PCT/US2016/023066, dated May 11, 2016.
International Search Report with Written Opinion corresponding to International Patent Application No. PCT/US2016/054424, dated Nov. 21, 2016.
Kim et al. (Apr. 9, 2011) "Discovery of novel HCV polymerase inhibitors using pharmacophore-based virtual screening," Bioorganic and Medicinal Chemistry. 21(11):3329-3334.

(56) References Cited

OTHER PUBLICATIONS

Lambeng et al. (2007) "Arylsulfonamides as a new class of cannabinoid CB1 receptor ligands: Identification of a lead and initial SAR studies," Bioorganic & Medicinal Chemistry Letters. 17(1):272-277.

Lau et al. (2005) "Peginterferon Alfa-2a, Lamivudine, and the Combination for HBeAg-Positive Chronic Hepatitis B," The New England Journal of Medicine. 352(26):2682-2695.

Liaw et al. (2009) "Hepatitis B virus infection," Lancet. 373:582-592.

Mabrouck (2012) "Discovering Best Candidates for Hepatocellular Carcinoma (HCC) by in-Silica Techniques and Tools," International Journal of Bioinformatics Research and Applications. 8(1-2):141-152.

Marcellin et al. (2004) "Peginterferon Alfa-2a Alone, Lamivudine Alone, and the Two in Combination in Patients with HBeAg-Negative Chronic Hepatitis B," New Engl. J. Med. 351(12):1206-1217.

Mohamed et al. (1986) "Synthesis of different types of chlorinated sulfonamides with expected insecticidal and antimicrobial activities," Acta Pharmaceutica Jugoslavica. 36(3):301-310.

Patani et al. (1996) "Bioisosterism: A Rational Approach in Drug Design," Chem. Rev. 96:3147-3176.

Patel et al. (2005) "Synthesis N-ethylpiperazinyl Sulfonyl Group Incorporated Benzamides" Indian Journal of Heterocyclic Chemistry. 15:201-202.

Search Report with Written Opinion corresponding to Singapore Patent Application No. 11201402660Y, completed May 22, 2015.

Supplementary European Search Report corresponding to European Patent Application No. 12859684, dated May 27, 2015.

Taylor et al. (Mar. 3, 2011) "A Brain-Permeable Small Molecule Reduces Neuronal Cholesterol by Inhibiting Activity of Sirtuin 2 Deacetylase," ACS Chemical Biology. 6:540-546.

The Merck Index (2013) "Infliximab," An Encyclopedia of Chemicals, Drugs and Biologicals. 14th Ed. p. 924.

\* cited by examiner

CRYSTALLINE FORMS OF A HEPATITIS B ANTIVIRAL AGENT

RELATED APPLICATIONS

This application claims priority to U.S. Provisional Application No. 62/234,124, filed Sep. 29, 2015, the content of which is incorporated herein in its entirety.

TECHNICAL FIELD

This disclosure relates to crystalline forms of 4-fluoro-3-((4-hydroxypiperidin-1-yl)sulfonyl)-N-(3,4,5-trifluorophenyl)benzamide, or hydrates or solvates thereof, and methods of making and using these forms.

BACKGROUND

The solid state of a compound can be important when the compound is used for pharmaceutical purposes. The physical properties of a compound can change from one solid form to another, which can affect the suitability of the form for pharmaceutical use. For example, a particular crystalline solid compound can overcome the disadvantage of other solid forms of the compound such as, e.g., instability and/or reduced purity.

Provided herein are solid crystalline forms of 4-fluoro-3-((4-hydroxypiperidin-1-yl)sulfonyl)-N-(3,4,5-trifluorophenyl)benzamide (also referred to herein as "a compound of Formula (1)" or "Compound (1)"). These crystalline forms of Compound (1) are advantageous in that they have low hygroscopicity, high purity, and high stability, making these forms suitable for use in pharmaceutical formulations.

SUMMARY

Provided herein are crystalline forms of a compound of Formula (1):

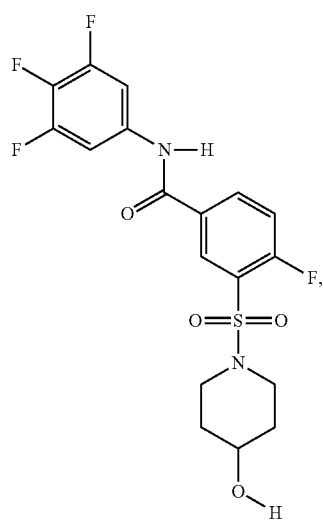

(1)

or hydrates or solvates thereof.

In an embodiment, the crystalline form of a compound of Formula (1) is anhydrous.

In an embodiment, the crystalline form of a compound of Formula (1) is characterized by an X-ray powder diffraction pattern having peaks expressed in degrees-2-theta at angles (±0.2°) of 18.0, 20.5, 21.9, 24.7, and 26.3 (Form I).

In an embodiment, the crystalline form of a compound of Formula (1) is characterized by an X-ray powder diffraction pattern having peaks expressed in degrees-2-theta at angles (±0.2°) of 9.9, 12.2, 15.1, 18.6, and 21.2 (Form III).

In an embodiment, the crystalline form of a compound of Formula (1) is characterized by an X-ray powder diffraction pattern having peaks expressed in degrees-2-theta at angles (±0.2°) of 10.9, 15.6, 16.1, 20.9, 24.9, and 27.2 (Form XII).

In an embodiment, the crystalline form of a compound of Formula (1) is characterized by an X-ray powder diffraction pattern having peaks expressed in degrees-2-theta at angles (±0.2°) of 17.1, 20.8, 22.2, 24.9, and 26.6 (Form XVI).

In an embodiment, the crystalline form of a compound of Formula (1) is characterized by a melting point at about 143° C.

In an embodiment, the crystalline form of a compound of Formula (1) is characterized by a melting point at about 143±2° C.

In an embodiment, the crystalline form of a compound of Formula (1) is characterized by a melting point at about 185° C.

In an embodiment, the crystalline form of a compound of Formula (1) is characterized by a melting point at about 185±2° C.

In an aspect, provided herein is a pharmaceutical composition comprising a crystalline form of the compound of Formula (1), or a hydrate or solvate thereof, and a pharmaceutically acceptable carrier.

In an embodiment of the pharmaceutical composition, the crystalline form is characterized by an X-ray powder diffraction pattern having peaks expressed in degrees-2-theta at angles (±0.2°) of 18.0, 20.5, 21.9, 24.7, and 26.3 (Form I).

In an embodiment of the pharmaceutical composition, the crystalline form is characterized by an X-ray powder diffraction pattern having peaks expressed in degrees-2-theta at angles (±0.2°) of 17.1, 20.8, 22.2, 24.9, and 26.6 (Form XVI).

In another aspect, provided herein is a method of treating an HBV infection in a subject in need thereof, comprising administering to the subject a therapeutically effective amount of the crystalline form of the compound of Formula (1), or a hydrate or solvate thereof.

In an embodiment of the method, the crystalline form is characterized by an X-ray powder diffraction pattern having peaks expressed in degrees-2-theta at angles (±0.2°) of 17.1, 20.8, 22.2, 24.9, and 26.6 (Form XVI).

In another aspect, provided herein is a crystalline form of the compound of Formula (1), formed by a process comprising:

(a) adding methyl tert-butyl ether (MTBE) to Compound (1) to form a slurry;
(b) stirring the slurry between about 20° C. and about 30° C.;
(c) filtering the slurry; and
(d) drying between about 50° C. and about 70° C., In an embodiment, the crystalline form is characterized by an X-ray powder diffraction pattern having peaks expressed in degrees-2-theta at angles (±0.2°) of 17.1, 20.8, 22.2, 24.9, and 26.6.

In an embodiment, Compound (1) of step (a) is a crystalline form characterized by an X-ray powder diffraction pattern having peaks expressed in degrees-2-theta at angles (±0.2°) of 9.9, 12.2, 15.1, 18.6, and 21.2.

In another embodiment, the crystalline form of the compound of Formula (1) is greater than 90% pure. In a further embodiment, the crystalline form of the compound of Formula (1) is greater than 95% pure. In yet a further embodiment, the crystalline form of the compound of Formula (1) is greater than 99% pure.

In an aspect, provided herein is a crystalline form of the compound of Formula (1), or a hydrate or solvate thereof, wherein the crystalline form is characterized by an X-ray powder diffraction pattern comprising peaks expressed in degrees-2-theta at angles (±0.2°) of 17.1, 22.2, 24.9, and 26.6.

In an embodiment, the crystalline form is characterized by a melting point at 185±2° C.

In an embodiment, the crystalline form is anhydrous.

In another aspect, provided herein is a crystalline form of the compound of Formula (1), or a hydrate or solvate thereof, wherein the crystalline form is characterized by a melting point at 185±2° C.

In an embodiment, the crystalline form is anhydrous.

DETAILED DESCRIPTION

Chronic hepatitis B virus (HBV) infection is a significant global health problem, affecting over 5% of the world population (over 350 million people worldwide and 1.25 million individuals in the U.S.). Thus, there is a need for compounds that can increase the suppression of virus production and that can treat HBV infection. One such compound is 4-fluoro-3-((4-hydroxypiperidin-1-yl)sulfonyl)-N-(3,4,5-trifluorophenyl)benzamide (CAS No. 1445790-55-5), shown as a compound of Formula (1) (also referred to herein as "Compound (1)"):

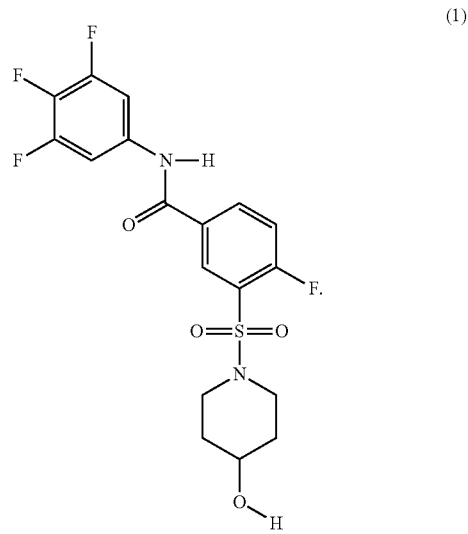 [SMILES: O=C(Nc1cc(F)c(F)c(F)c1)c1ccc(F)c(S(=O)(=O)N2CCC(O)CC2)c1]

(1)

The compound of Formula (1) is disclosed in PCT Publication No. WO/2013/096744 and U.S. Pat. No. 8,629,274, the entire contents of which are incorporated herein by reference.

The compound of Formula (1) can exist in amorphous solid forms or in crystalline solid forms. Crystalline solid forms of the compound of Formula (1) can exist in one or more unique polymorph forms. Accordingly, provided herein are crystalline forms of the compound of Formula (1), and compositions comprising these crystalline forms, in addition to various methods of preparing and using these compositions. These crystalline forms can be hydrates, solvates, or anhydrous forms of the compound of Formula (1). The preferred forms of the compound of Formula (1) are the anhydrous forms, e.g., Form I and Form XVI. In a more preferred form, the compound of Formula (1) is of the Form XVI.

Figure 10:
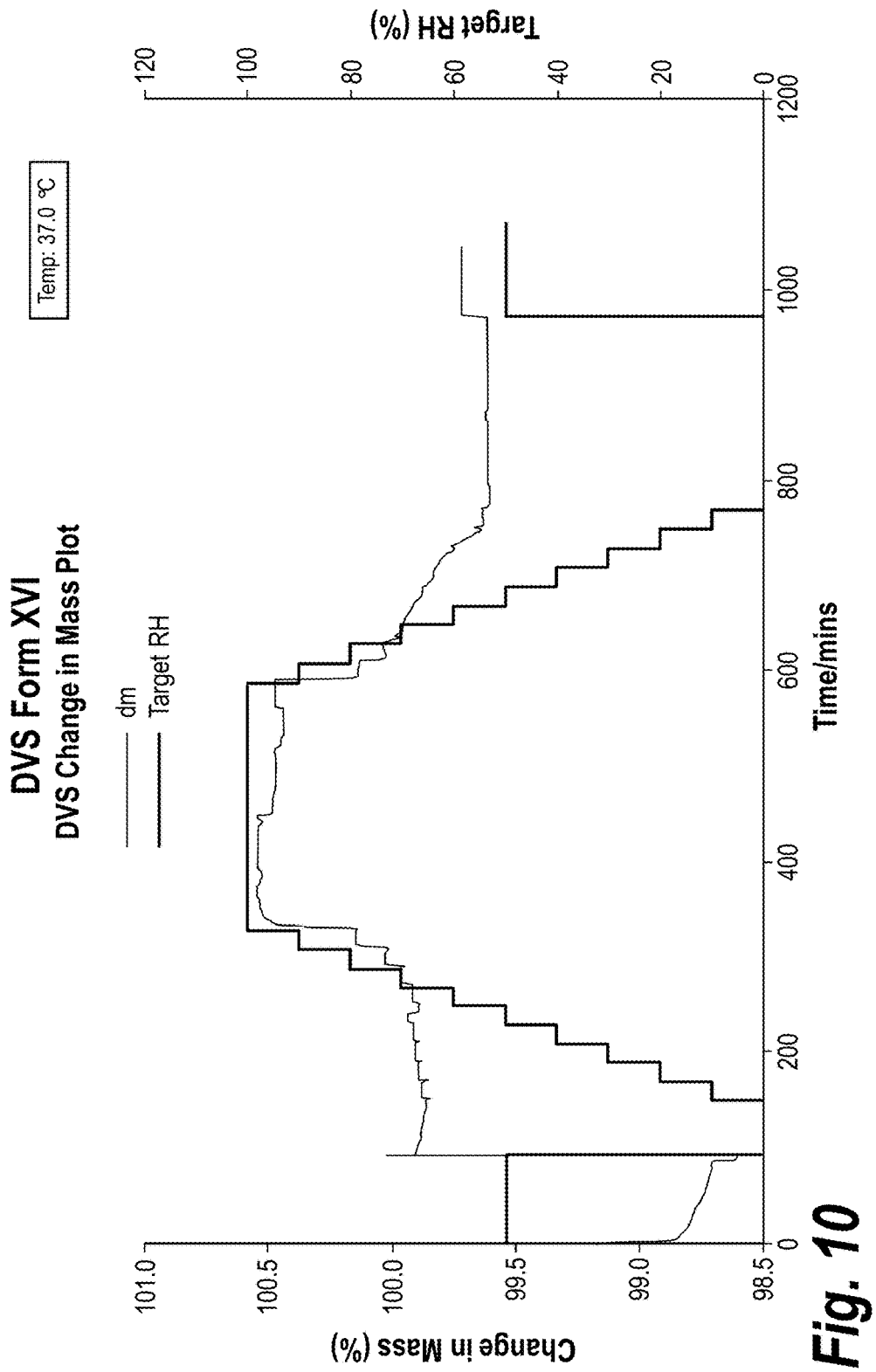
FIG. 10 shows the DVS graph of Form XVI.

A particular crystalline form of the compound of Formula (1) provided herein has advantageous characteristics that are beneficial to the preparation of various drug formulations. For example, a particular crystalline form of the compound of Formula (1), Form XVI, is a stable crystalline form. Form XVI maintains its crystallinity (i.e., is stable) upon exposure to higher temperatures and when subjected to varying relative humidity (see, e.g., Example 5 and FIGS. 12A-12B). Crystalline forms with good stability are important in the processes of preparation, packing, transportation, and storage of pharmaceutical products. Form XVI takes up up only 0.8% of water as determined by DVS carried out from 0% to 100% RH at 37° C. (see Example 5 and FIG. 10). The processes of making Form XVI (see, e.g., Example 3) also results in greater than 99% purity, an important feature for preparing and using pharmaceutical products.

The crystalline forms provided herein can be characterized by X-ray powder diffraction (XRPD), differential scanning calorimetry (DSC), and thermogravimetric analysis (TGA).

Polymorphism

The ability of a substance to exist in more than one solid form is defined as polymorphism; the different crystal forms of a particular substance are referred to as "polymorphs." In general, polymorphism is affected by the ability of a molecule of a substance to change its conformation or to form different intermolecular or intramolecular interactions, particularly hydrogen bonds, which is reflected in different atom arrangements in the crystal lattices of different polymorphs. In contrast, the overall external form of a substance is known as "morphology," which refers to the external shape of the crystal and the planes present, without reference to the internal structure. Crystals can display different morphology based on different conditions, such as, for example, growth rate, stirring, and the presence of impurities.

The different polymorphs of a substance can possess different energies of the crystal lattice and, thus, in solid state they can show different physical properties such as form, density, melting point, color, solubility, etc., which can, in turn, affect the stability, dissolution rate, and/or bioavailability of a given polymorph and its suitability for use as a pharmaceutical and in pharmaceutical compositions.

Access to different polymorphs of the compound of Formula (1) is desirable for other reasons as well. One such reason is that different polymorphs of a compound (e.g., the compound of Formula (1)) can incorporate different impurities, or chemical residues, upon crystallization. Certain polymorphs incorporate very little, or no, chemical residues. Accordingly, the formation of certain polymorph forms of a compound can result in purification of the compound.

Characterization of Polymorphs

In certain embodiments, the compounds of the invention are identifiable on the basis of characteristic peaks in an X-ray powder diffraction analysis. X-ray powder diffraction (XRPD) is a scientific technique using X-ray, neutron, or electron diffraction on powder, microcrystalline, or other solid materials for structural characterization of solid materials. A description of the methods used to obtain certain XRPD patterns in connection with the crystalline forms of the invention can be found in Example 6, Methods. In an embodiment, the X-ray powder diffraction data provided herein is obtained by a method utilizing Cu Kα radiation.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

1. Form I:

In one aspect, provided herein is 4-fluoro-3-((4-hydroxypiperidin-1-yl)sulfonyl)-N-(3,4,5-trifluorophenyl) benzamide of Form I (referred to herein as "Form I"). Form I (of Compound (1)) was determined to have a highly crystalline nature as determined by X-ray powder diffraction (XRPD) (see Example 2, and FIG. 1). Thermal characterization of the material was carried out by differential scanning calorimetry (DSC) and thermal gravimetric analysis (TGA) (see Example 5 and FIG. 2). The lack of weight loss during TGA indicates that Form I is an anhydrous crystalline form of Compound (1). The dynamic vapor sorption (DVS) experiment revealed 1.5% of moisture uptake (see Example 5 and FIG. 3), indicating the compound has low hydrophilicity (i.e., not very susceptible to water uptake). A stability test was performed by subjecting the sample to higher temperatures and humidity (see Example 5, FIGS. 11A-B).

In an embodiment, Form I is characterized by an X-ray powder diffraction pattern having peaks expressed in degrees-2-theta at angles (±0.2°) of 18.0, 20.5, 21.9, 24.7, and 26.3.

In another embodiment, Form I is characterized by an X-ray powder diffraction pattern having peaks expressed in degrees-2-theta at angles (±0.2°) of 14.1, 16.8, 18.0, 18.3, 19.2, 19.8, 20.5, 21.1, 21.9, 23.2, 24.7, and 26.3.

In yet a further embodiment, Form I is characterized by an X-ray powder diffraction pattern having peaks expressed in degrees-2-theta at angles (±0.2°) of 3.6, 6.3, 7.1, 7.9, 8.2, 10.7, 12.0, 12.6, 13.6, 14.1, 14.7, 15.6, 16.2, 16.8, 18.0, 18.3, 19.2, 19.8, 20.5, 21.1, 21.9, 23.2, 24.7, 25.9, 26.3, 27.4, 29.6, 30.3, 31.8, 34.5, 36.2, 38.2, and 41.5.

In yet a further embodiment, Form I is characterized by an X-ray powder diffraction pattern having peaks expressed in degrees-2-theta at angles (±0.2°) of 3.62, 6.33, 7.12, 7.87, 8.21, 10.66, 11.99, 12.64, 13.65, 14.10, 14.71, 15.58, 16.24, 16.80, 18.00, 18.31, 19.16, 19.81, 20.50, 21.11, 21.95, 23.16, 24.67, 25.87, 26.33, 27.40, 29.60, 30.28, 31.78, 34.50, 36.20, 38.20, and 41.53.

Figure 1:
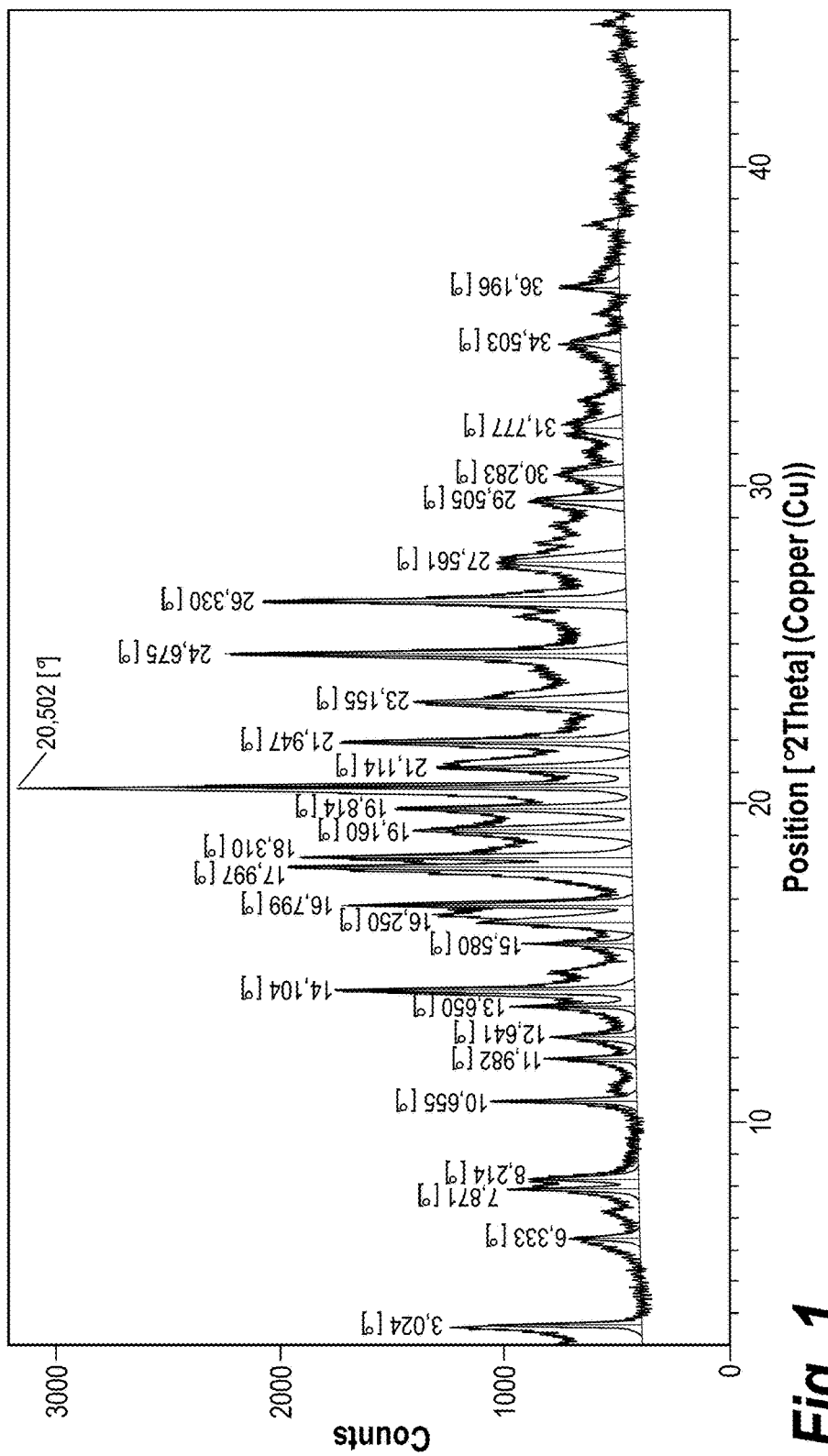
FIG. 1 shows the X-ray powder diffraction pattern of Form I of the compound of Formula (1).

In an embodiment, Form I is characterized by an X-ray powder diffraction pattern that is substantially the same as that of FIG. 1.

In another embodiment, Form I is characterized by a melting point at about 143° C. In a further embodiment, Form I is characterized by a melting point at 143±2° C. In an embodiment, the melting point is determined by DSC. In a further embodiment, Form I is characterized by a DSC thermogram that is substantially the same as that of FIG. 2.

2. Form III:

In one aspect, provided herein is 4-fluoro-3-((4-hydroxypiperidin-1-yl)sulfonyl)-N-(3,4,5-trifluorophenyl) benzamide of Form III (referred to herein as "Form III"). Form III (of Compound (1)) was characterized by X-ray powder diffraction (XRPD) (see Example 3, and FIG. 4). Form III has been determined to be a solvated form of 4-fluoro-3-((4-hydroxypiperidin-1-yl)sulfonyl)-N-(3,4,5-trifluorophenyl)benzamide, i.e., the acetone solvate of Compound (1) (See the TGA results, Example 3).

In an embodiment, Form III is characterized by an X-ray powder diffraction pattern having peaks expressed in degrees-2-theta at angles (±0.2°) of 9.9, 12.2, 15.1, 18.6, and 21.2.

In an embodiment, Form III is characterized by an X-ray powder diffraction pattern having peaks expressed in degrees-2-theta at angles (±0.2°) of 9.1, 9.9, 12.2, 15.1, 16.2, 18.3, 18.6, 21.2, 24.5, and 33.1.

In an embodiment, Form III is characterized by an X-ray powder diffraction pattern having peaks expressed in degrees-2-theta at angles (±0.2°) of 6.2, 9.1, 9.9, 10.0, 12.2, 13.0, 14.2, 15.1, 16.2, 16.9, 18.3, 18.6, 19.9, 21.2, 21.9, 22.2, 23.1, 24.5, 25.5, 25.8, 26.1, 26.7, 27.4, 28.1, 28.9, 30.0, 32.0, 33.1, 34.0, 34.4, 37.0, 38.3, 40.5, and 42.4.

In an embodiment, Form III is characterized by an X-ray powder diffraction pattern having peaks expressed in degrees-2-theta at angles (±0.2°) of 6.15, 9.08, 9.95, 10.03, 12.17, 12.96, 14.24, 15.15, 16.20, 16.88, 18.27, 18.64, 19.93, 21.20, 21.93, 22.25, 23.13, 24.48, 25.46, 25.84, 26.14, 26.75, 27.40, 28.05, 28.95, 30.01, 32.00, 33.09, 34.02, 34.40, 37.01, 38.34, 40.47, and 42.43.

Figure 4:
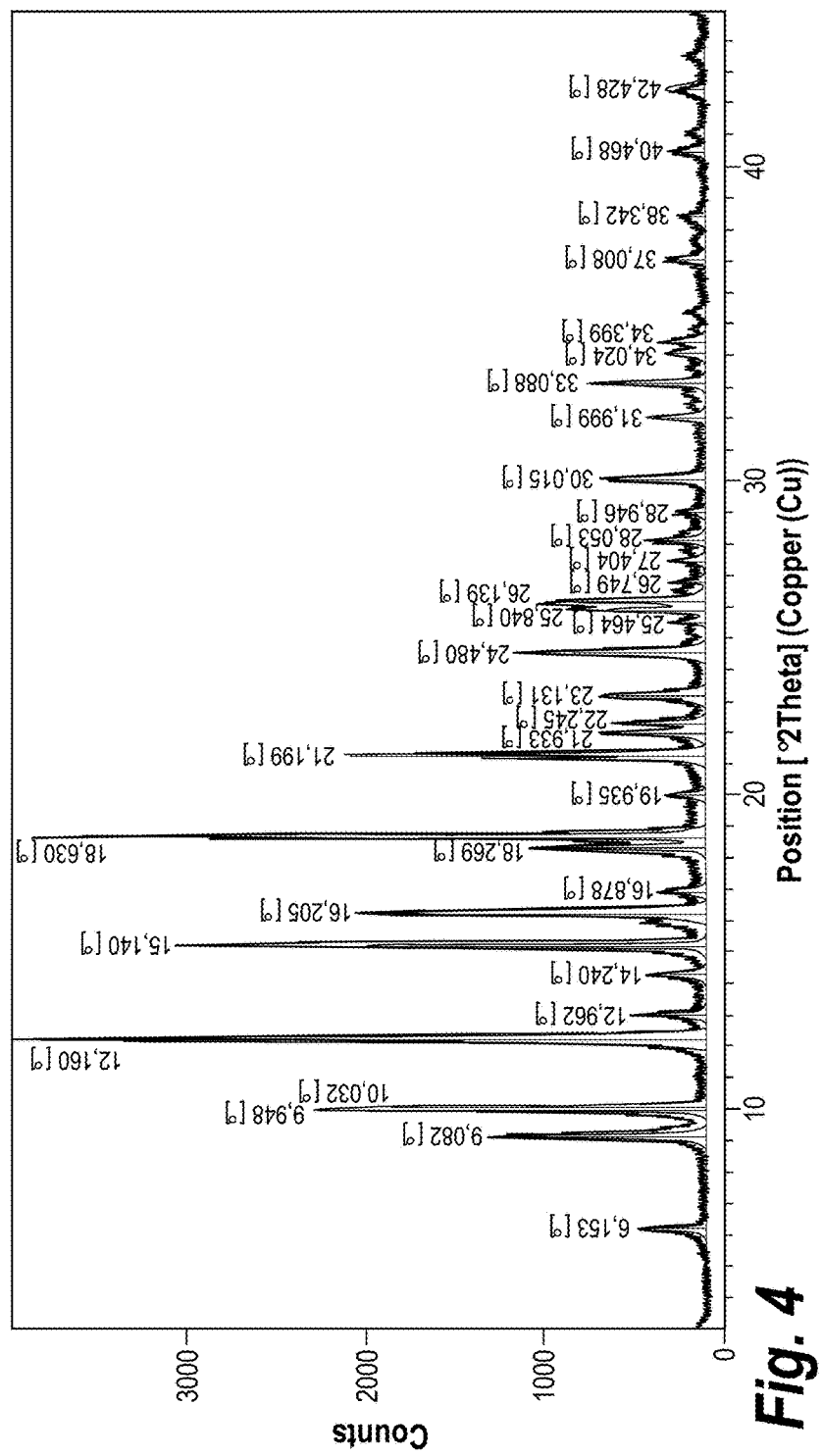
FIG. 4 shows the X-ray powder diffraction pattern of Form III of the compound of Formula (1).

In an embodiment, Form III is characterized by an X-ray powder diffraction pattern that is substantially the same as that of FIG. 4.

In another embodiment, Form III is characterized by a melting point at about 80° C. In a further embodiment, Form III is characterized by a melting point at 80±2° C. In an embodiment, the melting point is determined by DSC. In a further embodiment, Form III is characterized by a DSC thermogram that is substantially the same as that of FIG. 5.

3. Form XII:

In one aspect, provided herein is 4-fluoro-3-((4-hydroxypiperidin-1-yl)sulfonyl)-N-(3,4,5-trifluorophenyl)benzamide of Form XII (referred to herein as "Form XII"). Form XII (of Compound (1)) was characterized by X-ray powder diffraction (XRPD) (see Example 4, and FIG. 6). Form XII has been determined to be a hydrated form of crystalline 4-fluoro-3-((4-hydroxypiperidin-1-yl)sulfonyl)-N-(3,4,5-trifluorophenyl)benzamide (see the TGA, Example 4).

In an embodiment, Form XII is characterized by an X-ray powder diffraction pattern having peaks expressed in degrees-2-theta at angles (±0.2°) of 10.9, 15.6, 16.1, 20.9, 24.9, and 27.2.

In an embodiment, Form XII is characterized by an X-ray powder diffraction pattern having peaks expressed in degrees-2-theta at angles (±0.2°) of 10.9, 13.4, 15.6, 16.1, 17.1, 20.9, 22.1, 24.9 26.9, and 27.2.

In an embodiment, Form XII is characterized by an X-ray powder diffraction pattern having peaks expressed in degrees-2-theta at angles (±0.2°) of 8.1, 10.9, 12.9, 13.4, 14.1, 14.8, 15.1, 15.3, 15.6, 16.1, 17.1, 18.3, 19.1, 19.6, 20.9, 21.4, 22.1, 23.8, 24.1, 24.5, 24.9, 26.1, 26.9, 27.2, 28.1, 28.8, 29.5, 29.8, 30.1, 30.9, 31.4, 32.0, 33.3, 33.8, 34.1, 34.7, 35.2, 36.1, 37.7, 39.1, 39.6, 41.0, 41.6, and 42.5.

In another embodiment, Form XII is characterized by an X-ray powder diffraction pattern having peaks expressed in degrees-2-theta at angles (±0.2°) of 8.05, 10.93, 12.85, 13.37, 14.13, 14.83, 15.10, 15.35, 15.62, 16.08, 17.15, 18.31, 19.10, 19.62, 20.85, 21.43, 22.09, 23.77, 24.10, 24.48, 24.90, 24.95, 26.06, 26.89, 27.22, 28.10, 28.81, 29.50, 29.81, 30.11, 30.91, 31.42, 32.01, 33.27, 33.76, 34.06, 34.68, 35.16, 36.14, 37.67, 39.10, 39.61, 41.00, 41.59, and 42.50.

Figure 6:
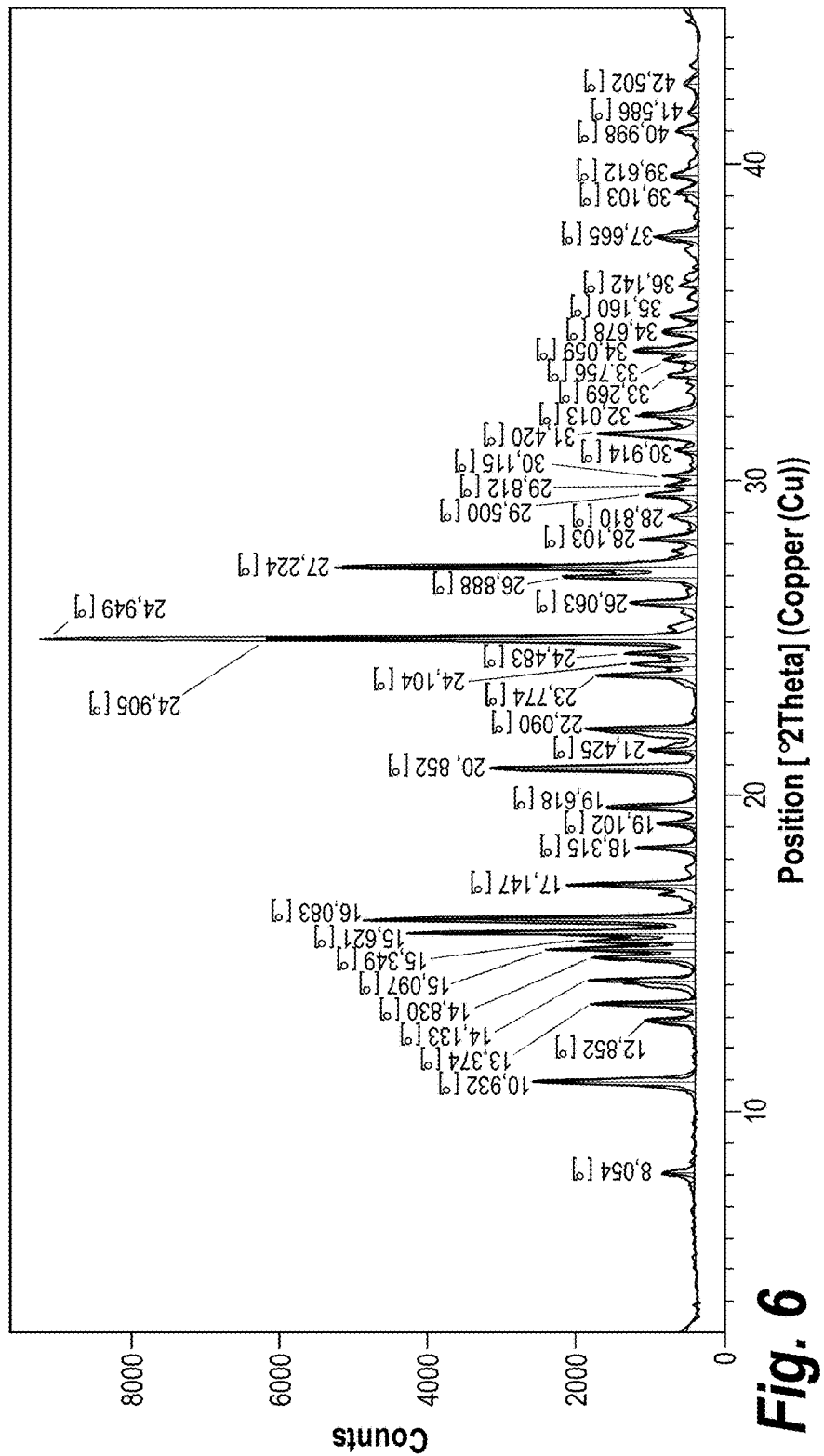
FIG. 6 shows the X-ray powder diffraction pattern of Form XII of the compound of Formula (1).

In an embodiment, Form XII is characterized by an X-ray powder diffraction pattern that is substantially the same as that of FIG. 6.

In another embodiment, Form XII is characterized by a melting point at about 100° C. In a further embodiment, Form XII is characterized by a melting point at 100±2° C. In an embodiment, the melting point is determined by DSC. In a further embodiment, Form XII is characterized by a DSC thermogram that is substantially the same as that of FIG. 7.

4. Form XVI:

In one aspect, provided herein is 4-fluoro-3-((4-hydroxypiperidin-1-yl)sulfonyl)-N-(3,4,5-trifluorophenyl)benzamide of Form XVI (referred to herein as "Form XVI"). Form XVI (of Compound (1)) was determined to have a highly crystalline nature as determined by X-ray powder diffraction (XRPD) (see Example 3 and FIG. 8, as well as Example 8). Further, Form XVI is an anhydrous crystalline form of Compound (1) evidenced by a lack of weight loss upon study by TGA (See Example 5 and FIG. 9). The dynamic vapor sorption (DVS) experiment revealed 0.8% of moisture uptake (see Example 5 and FIG. 10), indicating that the compound has low hydrophilicity (i.e., not susceptible to water uptake). A stability test was performed by subjecting the sample to higher temperatures and humidity (see Example 5, FIGS. 12A-B) and monitoring the XRPD of the material. Form XVI was shown to be a highly stable crystalline form of Compound (1).

In an embodiment, Form XVI is characterized by an X-ray powder diffraction pattern having peaks expressed in degrees-2-theta at angles (±0.2°) of 17.1, 22.2, 24.9, and 26.6.

In an embodiment, Form XVI is characterized by an X-ray powder diffraction pattern having peaks expressed in degrees-2-theta at angles (±0.2°) of 17.1, 20.8, 22.2, 24.9, and 26.6.

In an embodiment, Form XVI is characterized by an X-ray powder diffraction pattern having peaks expressed in degrees-2-theta at angles (±0.2°) of 14.4, 17.1, 18.5, 20.0, 20.8, 22.2, 23.4, 24.9, 26.6, 28.0, and 36.4.

In an embodiment, Form XVI is characterized by an X-ray powder diffraction pattern having peaks expressed in degrees-2-theta at angles (±0.2°) of 8.3, 10.9, 14.4, 14.9, 15.8, 16.5, 17.1, 18.5, 18.9, 20.0, 20.8, 21.6, 22.2, 22.8, 23.4, 23.6, 24.9, 26.6, 28.0, 28.4, 29.6, 29.8, 30.5, 31.2, 31.7, 32.9, 34.2, 34.5, 35.6, 36.4, 36.8, 38.4, 39.7, 40.2, 41.7, 43.6, and 44.7.

In an embodiment, Form XVI is characterized by an X-ray powder diffraction pattern having peaks express in degrees-2-theta at angles (±0.2°) of 8.33, 10.93, 14.37, 14.92, 15.84, 16.46, 17.07, 18.53, 18.90, 20.02, 20.77, 21.60, 22.16, 22.83, 23.44, 23.63, 24.93, 26.60, 28.00, 28.38, 29.56, 29.77, 30.45, 31.20, 31.70, 32.93, 34.16, 34.54, 35.60, 36.37, 36.75, 38.37, 39.71, 40.17, 41.71, 43.64, and 44.69.

Figure 8:
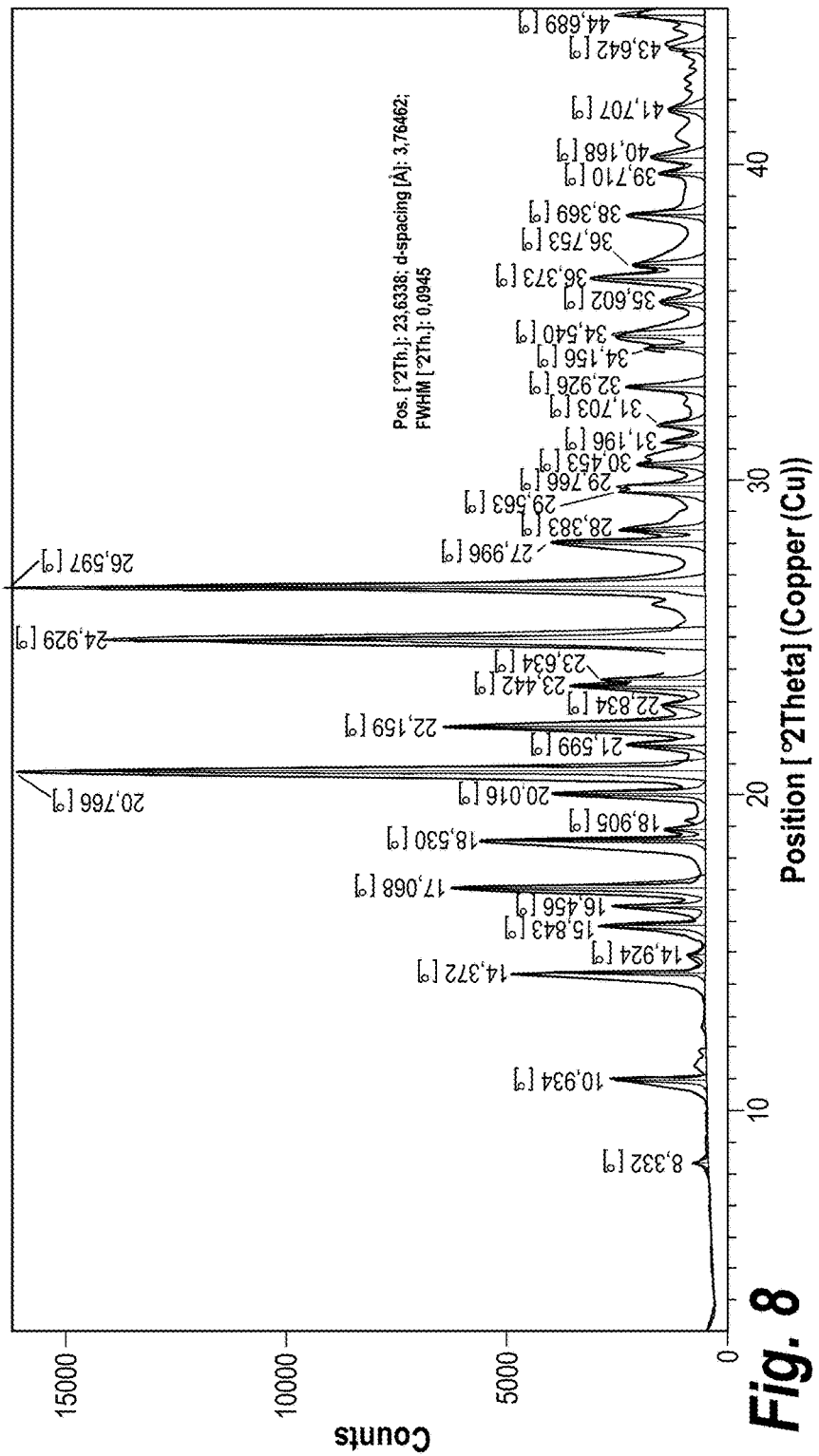
FIG. 8 shows the X-ray powder diffraction pattern of Form XVI of the compound of Formula (1).

In an embodiment, Form XVI is characterized by an X-ray powder diffraction pattern that is substantially the same as that of FIG. 8. In an embodiment, Form XVI is characterized by an X-ray powder diffraction pattern that is substantially the same as that of FIG. 14A. In an embodiment, Form XVI is characterized by an X-ray powder diffraction pattern that is substantially the same as that of FIG. 14B.

In another embodiment, Form XVI is characterized by a melting point at about 185° C. In a further embodiment, Form XVI is characterized by a melting point at 185±2° C. In an embodiment, the melting point is determined by DSC. In a further embodiment, Form XVI is characterized by a DSC thermogram that is substantially the same as that of FIG. 9.

In an aspect, provided herein is a crystalline form of Compound (1) characterized by an X-ray powder diffraction pattern comprising peaks expressed in degrees-2-theta at angles (±0.2°) of 17.1, 22.2, 24.9, and 26.6. In an embodiment of this aspect, the crystalline form of Compound (1) is characterized by a melting point at 185±2° C. In a further embodiment, the crystalline form is anhydrous.

In another aspect, provided herein is a crystalline form of the compound of Formula (1), or a hydrate or solvate thereof, wherein the crystalline form is characterized by a melting point at 185±2° C. In an embodiment, the crystalline form is anhydrous.

Processes and Methods

Provided herein are processes or methods of making crystalline forms of 4-fluoro-3-((4-hydroxypiperidin-1-yl)sulfonyl)-N-(3,4,5-trifluorophenyl)benzamide or Compound (1).

In one aspect, provided herein is a process for preparing Compound (1) comprising reacting compound 3:

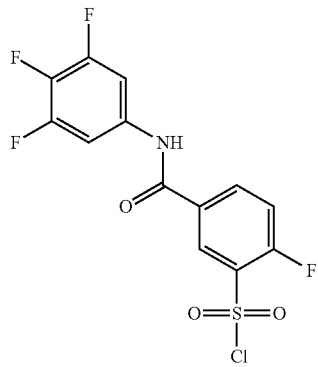

with 4-hydroxypiperidine and triethylamine in acetone.

In an embodiment, Compound (1) is of Form III (i.e., the acetone solvate).

In a further embodiment of the process, compound 3 is prepared by a process comprising reacting compound 2:

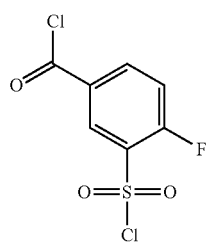

with trifluoroaniline at reflux.

In a further embodiment (of preparing compound 3), compound 2 is prepared by a process comprising reacting compound 1a:

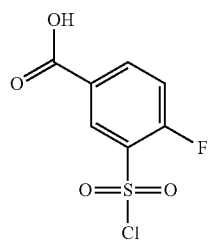

with SOCl$_2$ in toluene.

In an embodiment of the process of preparing compound 2, SOCl$_2$ is added in an amount of between about 2 and about 3 equivalents with respect to compound 1a. In a further embodiment of the process of preparing compound 2, DMF (dimethylformamide) is added in a catalytic amount.

In an aspect, provided herein is a process of preparing compound 2:

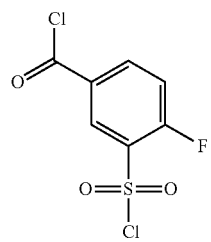

comprising reacting compound 1a:

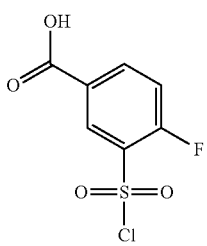

with SOCl$_2$ in toluene, wherein the SOCl$_2$ is present in an amount of between about 2 and about 3 equivalents with respect to compound 1a. In an embodiment of the process of preparing compound 2, the process comprises adding DMF in a catalytic amount.

In one aspect, provided herein is a process for making Form III of Compound (1) comprising the following steps:

(a) adding acetone to Compound (1);
(b) adding water;
(c) filtering the solution of step (b);
(d) cooling the solution;
(e) adding water;
(f) cooling the solution;
(g) forming a slurry with acetone:water 50:50; and
(h) filtering the slurry formed in step (g) to obtain a solid comprising Form III.

In an embodiment, the solution of step (d) is seeded with between about 0.1% and 1% of Form III of Compound (1). In a further embodiment, the solution can be seeded with about 1% or 0.1% of Form III of Compound (1).

In an embodiment, step (a) is carried out at about 45° C. In another embodiment, step (c) is carried out at about 45° C. In another embodiment, the solution of step (d) is cooled to about 20° C. In another embodiment, the solution of step (f) is cooled to about 10° C. In another embodiment, step (g) is carried out at about 10° C.

In another embodiment, the process for making making Form III further comprises step (i), washing the solid obtained in step (h) with a acetone:water 50/50 at about 10° C. In another embodiment, the process further comprises drying the solid obtained from either steps (h) or (i) at about 50° C. under vacuum.

In another aspect, provided herein is a process for making an anhydrous form of Compound (1), comprising the following steps:

(a) adding methyl tert-butyl ether (MTBE) to Form III of Compound (1) to form a slurry;

(b) stirring the slurry;

(c) filtering the slurry; and (d) drying the resulting solid.

In an embodiment, step (b) is carried out between about 20° C. and 30° C.

In another aspect, provided herein is a process for making Form I of Compound (1), comprising the following steps:

(a) adding methyl tert-butyl ether (MTBE) to Form III of Compound (1) to form a slurry;

(b) stirring the slurry;

(c) filtering the slurry; and (d) drying the resulting solid at about 30° C.

In an embodiment, step (b) is carried out between about 20° C. and 30° C. In an embodiment, the resulting Form I of Compound (1) can be manually milled and sieved. In an embodiment, the purity of Compound (1) of Form I is greater than 90%. In an embodiment, the purity of Compound (1) of Form I is greater than 95%. In an embodiment, the purity of Compound (1) of Form I is greater than 99%. The purity of Compound (1) of Form I can be measured by HPLC (see, e.g., the HPLC method described in Example 2, Section I).

In another aspect, provided herein is a process for making Form XVI of Compound (1), comprising the following steps:

(a) adding methyl tert-butyl ether (MTBE) to Form III of Compound (1) to form a slurry;

(b) stirring the slurry;

(c) filtering the slurry; and (d) drying the resulting solid between about 50° C. and about 70° C.

In an embodiment, step (b) is carried out between about 20° C. and about 30° C. In a further embodiment, the resulting Form XVI of Compound (1) can be manually milled and sieved. In an embodiment, the purity of Compound (1) of Form XVI is greater than 90%. In an embodiment, the purity of Compound (1) of Form XVI is greater than 95%. In an embodiment, the purity of Compound (1) of Form XVI is greater than 99%. The purity of Compound (1) of Form XVI can be measured by HPLC (see, e.g., the HPLC method described in Example 2, Section I).

In an embodiment of the processes provided herein, Form III is characterized by an X-ray powder diffraction pattern having peaks expressed in degrees-2-theta at angles (±0.2°) of 9.9, 12.2, 15.1, 18.6, and 21.2; and Form XVI is characterized by an X-ray powder diffraction pattern having peaks expressed in degrees-2-theta at angles (±0.2°) of 17.1, 20.8, 22.2, 24.9, and 26.6.

In another aspect, provided herein is a crystalline form of the compound of Formula (1)

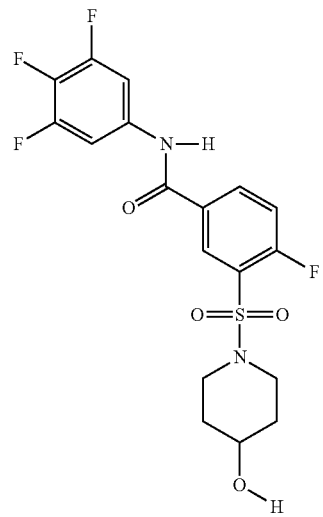

(1)

formed by a process comprising:

(a) adding methyl tert-butyl ether (MTBE) to Compound (1) to form a slurry;

(b) stirring the slurry between about 20° C. and about 30° C.;

(c) filtering the slurry; and (d) drying between about 50° C. and about 70° C.

In an embodiment, the resulting crystalline form is characterized by an X-ray powder diffraction pattern having peaks expressed in degrees-2-theta at angles (±0.2°) of 17.1, 20.8, 22.2, 24.9, and 26.6 (i.e., Form XVI of Compound (1)).

In another embodiment, Compound (1) of step (a) is a crystalline form characterized by an X-ray powder diffraction pattern having peaks expressed in degrees-2-theta at angles (±0.2°) of (±0.2°) of 9.9, 12.2, 15.1, 18.6, and 21.2 (i.e., Form III of Compound (1)).

In an embodiment, Form III is prepared by the process described above, the processes described in Examples 1, 2, or 3, or any reasonable combination and/or variation thereof.

In another aspect, provided herein is a crystalline form of the compound of Formula (1)

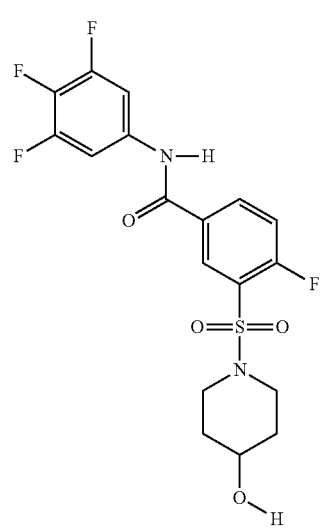

(1)

formed by a process comprising:

(a) adding isopropyl alcohol to Compound (1) to form a solution;

(b) stirring the solution between about 50° C. and about 60° C.;

(c) adding n-heptane;

(d) reducing the temperature to between about 35° C. and about 45° C. and stirring;

(e) filtering the solution to obtain a solid; and (f) drying between about 25° C. and about 60° C.

In an embodiment, the resulting crystalline form is characterized by an X-ray powder diffraction pattern having peaks expressed in degrees-2-theta at angles (±0.2°) of 17.1, 22.2, 24.9, and 26.6 (i.e., Form XVI of Compound (1)).

Pharmaceutical Compositions

Provided herein are pharmaceutical compositions or formulations comprising one or more crystalline forms of Compound (1). The pharmaceutical compositions provided herein can contain one or more of the crystalline forms of Compound (1) (i.e., Forms I, III, XII, and/or XVI).

In certain embodiments, the pharmaceutical compositions will comprise a crystalline form of Compound (1) that is substantially free from other crystalline forms.

Thus, provided herein is a pharmaceutical composition comprising Form I of Compound (1) and a pharmaceutically acceptable carrier, wherein Form I is substantially free of other crystalline forms of Compound (1) (e.g., substantially free of Forms III, XII, and XVI). Also provided herein is a pharmaceutical composition comprising Form XVI of Compound (1) and a pharmaceutically acceptable carrier, wherein Form XVI is substantially free of other crystalline forms of Compound (1) (e.g., substantially free of Forms I, III, and XII).

In an aspect, provided herein is a pharmaceutical composition comprising Compound (1) of Form I and a pharmaceutically acceptable carrier, wherein Form I is characterized by an X-ray powder diffraction pattern having peaks expressed in degrees-2-theta at angles (±0.2°) of 18.0, 20.5, 21.9, 24.7, and 26.3. In an embodiment, Compound (1) is substantially free of crystalline forms other than Form I. In another embodiment, Compound (1) is greater than 90% pure. In yet another embodiment, Compound (1) is greater than 95% pure. In another embodiment, Compound (1) is greater than 99% pure. The purity of Compound (1) can be determined by HPLC, such as the method described in Example 2, Section I.

In another aspect, provided herein is a pharmaceutical composition comprising Compound (1) of Form XVI and a pharmaceutically acceptable carrier, wherein Form XVI is characterized by an X-ray powder diffraction pattern having peaks expressed in degrees-2-theta at angles (±0.2°) of 17.1, 20.8, 22.2, 24.9, and 26.6. In an embodiment, Compound (1) is substantially free of crystalline forms other than Form XVI. In another embodiment, Compound (1) is greater than 90% pure. In yet another embodiment, Compound (1) is greater than 95% pure. In another embodiment, Compound (1) is greater than 99% pure.

The purity of Compound (1) can be determined by HPLC, such as the method described in Example 2, Section 1.

The pharmaceutical compositions can be formulated for oral, intravenous, intramuscular, subcutaneous or parenteral administration for the therapeutic or prophylactic treatment of diseases, such as a hepatitis B infection.

The pharmaceutical preparations disclosed herein can be prepared in accordance with standard procedures and are administered at dosages that are selected to reduce, prevent or eliminate disease (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various agents for human therapy).

The pharmaceutical compositions can comprise one or more of the crystalline forms disclosed herein in association with one or more nontoxic, pharmaceutically-acceptable carriers and/or diluents and/or adjuvants and/or excipients. In a preferred embodiment, the pharmaceutical composition comprises Form I or Form XVI.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

For oral or parenteral administration, the crystalline forms disclosed herein can be mixed with conventional pharmaceutical carriers and excipients and used in the form of tablets, capsules, elixirs, suspensions, syrups, wafers and the like. The compositions comprising a compound of this invention can contain from about 0.1% to about 99% by weight of the active compound, such as from about 10% to about 30%.

For oral use, solid formulations such as tablets and capsules are useful. Sustained release or enterically coated preparations can also be devised. For pediatric and geriatric applications, one embodiment provides suspensions, syrups and chewable tablets. For oral administration, the pharmaceutical compositions are in the form of, for example, a tablet, capsule, suspension or liquid.

The pharmaceutical compositions can be made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, fillers, lubricants, disintegrants, or acceptable wetting agents. Oral liquid preparations generally are in the form of aqueous or oily solutions, suspensions, emulsions, syrups or elixirs.

The pharmaceutical compositions disclosed herein can be placed in a pharmaceutically acceptable carrier and are delivered to a recipient subject (e.g., a human) in accordance with known methods of drug delivery. In general, the methods of delivering the pharmaceutical compositions in vivo utilize art-recognized protocols for delivering the agent with the only substantial procedural modification being the substitution of the compounds of the present invention for the drugs in the art-recognized protocols.

As used herein, the phrases "therapeutically-effective dose" and "therapeutically-effective amount" refer to an amount of a compound that prevents the onset, alleviates the symptoms, stops the progression of a disease, or results in another desired biological outcome such as, e.g., improved clinical signs. The term "treating" or "treatment" is defined as administering, to a subject, a therapeutically-effective amount of one or more compounds to control or eliminate a disease. Those in need of treatment can include individuals already having a particular medical disease as well as those at risk for the disease (i.e., those who are likely to ultimately acquire the disease or disorder). The term "subject," as used herein, refers to a mammal, a plant, a lower animal, or a cell culture. In one embodiment, a subject is a human or other animal patient in need of treatment.

The term "administering" or "administration" and the like, refers to providing Compound (1) to the subject in need of treatment. Preferably the subject is a mammal, more preferably a human.

Methods of Treating

Provided herein are methods for the treatment of a disease comprising administering one or more crystalline forms of Compound (1), or a pharmaceutical composition comprising one or more crystalline forms of Compound (1).

In one aspect, provided herein is a method of treating an HBV infection in a subject in need thereof, comprising administering to the subject a therapeutically effective amount of the crystalline form of the compound of Formula (1)

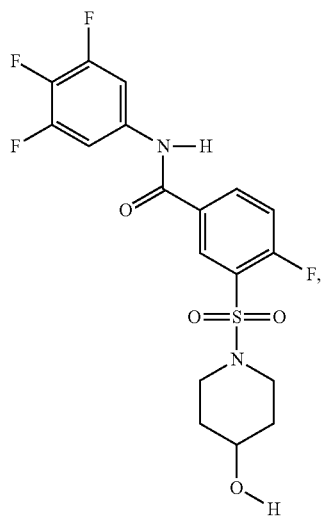

(I)

or a hydrate or solvate thereof.

In one aspect, provided herein is a method of treating an HBV infection in a subject in need thereof, comprising administering to the subject a therapeutically effective amount of a crystalline form of Compound (1).

In another aspect, provided herein is a method of reducing viral load associated with an HBV infection in a subject in need thereof, comprising administering to the individual a therapeutically effective amount of a crystalline form of Compound (1).

In another aspect, provided herein is a method of reducing reoccurrence of an HBV infection in a subject in need thereof, comprising administering to the subject a therapeutically effective amount of a crystalline form of Compound (1).

In another aspect, provided herein is a method of reducing the physiological impact of an HBV infection in a subject in need thereof, comprising administering to the subject a therapeutically effective amount of a crystalline form of Compound (1).

In another aspect, provided herein is a method of reducing, slowing, or inhibiting an HBV infection in a subject in need thereof, comprising administering to the subject a therapeutically effective amount of a crystalline form of Compound (1).

In another aspect, provided herein is a method of inducing remission of hepatic injury from an HBV infection in a subject in need thereof, comprising administering to the subject a therapeutically effective amount of a crystalline form of Compound (1).

In another aspect, provided herein is a method of reducing the physiological impact of long-term antiviral therapy for HBV infection in a subject in need thereof, comprising administering to the subject a therapeutically effective amount of a crystalline form of Compound (1).

In another aspect, provided herein is a method of eradicating an HBV infection in a subject in need thereof, comprising administering to the subject a therapeutically effective amount of a crystalline form of Compound (1).

In another aspect, provided herein is a method of prophylactically treating an HBV infection in a subject in need thereof, wherein the subject is afflicted with a latent HBV infection, comprising administering to the subject a therapeutically effective amount of a crystalline form of Compound (1).

In an embodiment of the methods provided herein, the crystalline form of Compound (1) is of Form I or Form XVI. In a preferred embodiment of the methods provided herein, the crystalline form of Compound (1) is of Form XVI.

In another aspect, provided herein is a method of treating an HBV infection in a subject in need thereof, comprising administering to the subject a therapeutically effective amount of a crystalline form of Compound (1), wherein the form is characterized by an X-ray powder diffraction pattern having peaks expressed in degrees-2-theta at angles (±0.2°) of 17.1, 20.8, 22.2, 24.9, and 26.6 (Form XVI).

In another aspect, provided herein is a method of reducing viral load associated with an HBV infection in a subject in need thereof, comprising administering to the subject a therapeutically effective amount of a crystalline form of Compound (1), wherein the form is characterized by an X-ray powder diffraction pattern having peaks expressed in degrees-2-theta at angles (±0.2°) of 17.1, 20.8, 22.2, 24.9, and 26.6 (Form XVI).

In another aspect, provided herein is a method of reducing reoccurrence of an HBV infection in a subject in need thereof, comprising administering to the subject a therapeutically effective amount of a crystalline form of Compound (1), wherein the form is characterized by an X-ray powder diffraction pattern having peaks expressed in degrees-2-theta at angles (±0.2°) of 17.1, 20.8, 22.2, 24.9, and 26.6 (Form XVI).

In another aspect, provided herein is a method of reducing the physiological impact of an HBV infection in a subject in need thereof, comprising administering to the subject a therapeutically effective amount of a crystalline form of Compound (1), wherein the form is characterized by an X-ray powder diffraction pattern having peaks expressed in degrees-2-theta at angles (±0.2°) of 17.1, 20.8, 22.2, 24.9, and 26.6 (Form XVI).

In another aspect, provided herein is a method of reducing, slowing, or inhibiting an HBV infection in a subject in need thereof, comprising administering to the subject a therapeutically effective amount of a crystalline form of Compound (1), wherein the form is characterized by an X-ray powder diffraction pattern having peaks expressed in degrees-2-theta at angles (±0.2°) of 17.1, 20.8, 22.2, 24.9, and 26.6 (Form XVI).

In another aspect, provided herein is a method of inducing remission of hepatic injury from an HBV infection in a subject in need thereof, comprising administering to the subject a therapeutically effective amount of a crystalline form of Compound (1), wherein the form is characterized by an X-ray powder diffraction pattern having peaks expressed in degrees-2-theta at angles (±0.2°) of 17.1, 20.8, 22.2, 24.9, and 26.6 (Form XVI).

In another aspect, provided herein is a method of reducing the physiological impact of long-term antiviral therapy for HBV infection in a subject in need thereof, comprising administering to the subject a therapeutically effective amount of a crystalline form of Compound (1), wherein the form is characterized by an X-ray powder diffraction pattern having peaks expressed in degrees-2-theta at angles (±0.2°) of 17.1, 20.8, 22.2, 24.9, and 26.6 (Form XVI).

In another aspect, provided herein is a method of eradicating an HBV infection in a subject in need thereof, comprising administering to the subject a therapeutically effective amount of a crystalline form of Compound (1), wherein the form is characterized by an X-ray powder diffraction pattern having peaks expressed in degrees-2-theta at angles (±0.2°) of 17.1, 20.8, 22.2, 24.9, and 26.6 (Form XVI).

In another aspect, provided herein is a method of prophylactically treating an HBV infection in a subject in need thereof, wherein the subject is afflicted with a latent HBV infection, comprising administering to the subject a therapeutically effective amount of a crystalline form of Compound (1), wherein the form is characterized by an X-ray powder diffraction pattern having peaks expressed in degrees-2-theta at angles (±0.2°) of 17.1, 20.8, 22.2, 24.9, and 26.6 (Form XVI).

Combination Therapies

The crystalline forms of Compound (1) can be useful in combination with one or more additional compounds useful for treating HBV infection. These additional compounds may comprise compounds of the present invention or compounds known to treat, prevent, or reduce the symptoms or effects of HBV infection. Such compounds include but are not limited to HBV polymerase inhibitors, interferons, viral entry inhibitors, viral maturation inhibitors, literature-described capsid assembly modulators, reverse transcriptase inhibitor, immunomodulatory agents, a TLR-agonist, and other agents with distinct or unknown mechanisms that affect the HBV life cycle and/or affect the consequences of HBV infection.

In non-limiting examples, the crystalline forms of Compound (1) may be used in combination with one or more drugs (or a salt thereof) selected from the group consisting of HBV reverse transcriptase inhibitors, and DNA and RNA polymerase inhibitors, including but not limited to: lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons, including but not limited to interferon alpha (IFN-α), interferon beta (IFN-β), interferon lambda (IFN-λ), and interferon gamma (IFN-γ);

viral entry inhibitors;

viral maturation inhibitors;

literature-described capsid assembly modulators, such as, but not limited to BAY 41-4109;

reverse transcriptase inhibitor;

an immunomodulatory agent such as a TLR-agonist; and agents of distinct or unknown mechanism, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In one embodiment, the additional therapeutic agent is an interferon. The term "interferon" or "IFN" refers to any member the family of highly homologous species-specific proteins that inhibit viral replication and cellular proliferation, and modulate immune response. Human interferons are grouped into three classes; Type I, which include interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons include pegylated interferons and glycosylated interferons. Examples of interferons also include, but are not limited to, interferon-alpha-2a, interferon-alpha-2b, interferon-alpha-n1, interferon-beta-1a, interferon-beta-1b, interferon-lamda-1, interferon-lamda-2, and interferon-lamda-3. Examples of pegylated interferons include pegylated interferon-alpha-2a and pegylated interferon alpha-2b.

Accordingly, in one embodiment, the crystalline forms of Compound (1) (e.g., Form I and Form XVI) can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS).

In another embodiment, the additional therapeutic agent is selected from immune modulator or immune stimulator therapies, which includes biological agents belonging to the interferon class.

Further, the additional therapeutic agent may be an agent of distinct or unknown mechanism including agents that disrupt the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor and/or DNA and/or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In an embodiment, the additional therapeutic agent is an immunomodulatory agent that induces a natural, limited immune response leading to induction of immune responses against unrelated viruses. In other words, the immunomodulatory agent can effect maturation of antigen presenting cells, proliferation of T-cells and cytokine release (e.g., IL-12, IL-18, IFN-alpha, -beta, and -gamma and TNF-alpha among others), In a further embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl] acetate).

In any of the methods provided herein, the method may further comprise administering to the individual at least one HBV vaccine, a nucleoside HBV inhibitor, an interferon or any combination thereof. In an embodiment, the HBV vaccine is at least one of RECOMBIVAX HB, ENGERIX-B, ELOVAC B, GENEVAC-B, or SHANVAC B.

In another aspect, provided herein is method of treating an HBV infection in an individual in need thereof, comprising reducing the HBV viral load by administering to the individual a therapeutically effective amount of a crystalline form of Compound (1) alone or in combination with a reverse transcriptase inhibitor; and further administering to the individual a therapeutically effective amount of HBV vaccine. The reverse transcriptase inhibitor may be one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.
In an embodiment of any of the methods of administering combination therapies provided herein, the method can further comprise monitoring the HBV viral load of the subject, wherein the method is carried out for a period of time such that the HBV virus is undetectable.

The following examples further illustrate aspects of the present invention. However, they are in no way a limitation of the teachings or disclosure of the present invention as set forth herein.

EXAMPLES

Example 1

Synthesis of Compound (1)

I. Disclosed Synthesis

The following synthesis is disclosed in PCT Publication No. WO/2013/096744, which is incorporated herein by reference in its entirety.

Reaction Scheme:

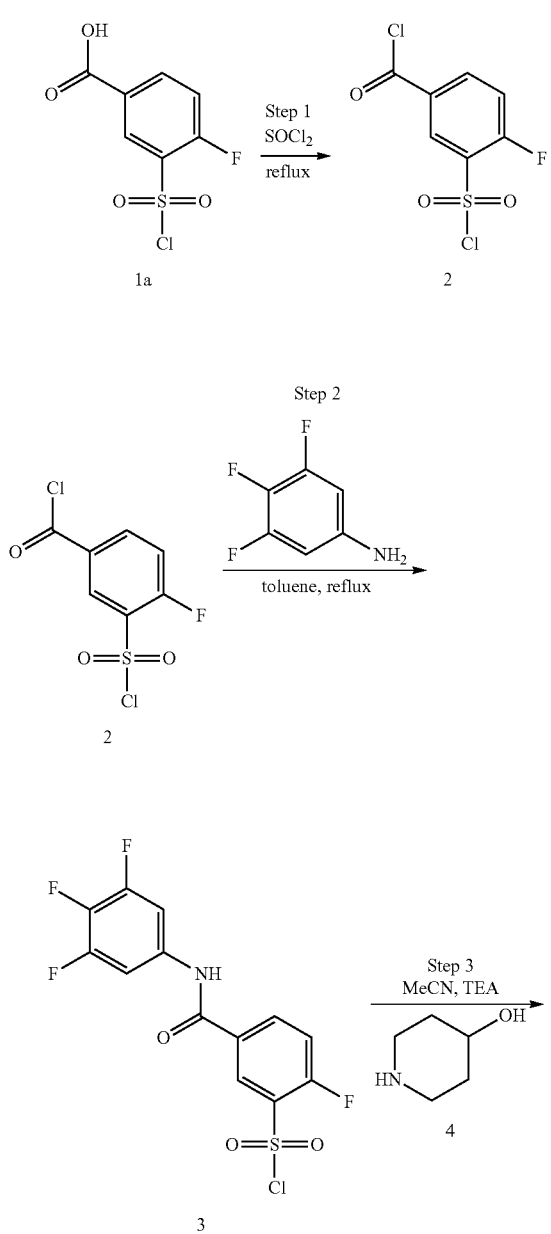

-continued

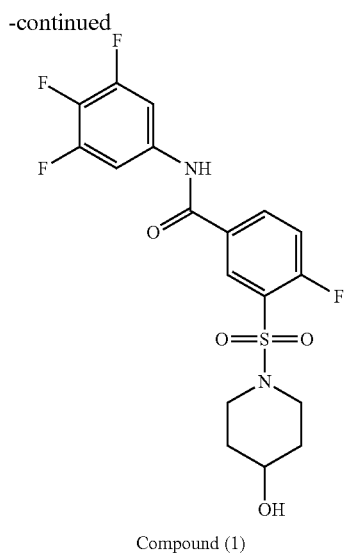

Compound (1)

Step 1: Preparation of Compound 2

A mixture of compound 1a (10.0 g, 42.0 mmol) in SOCl$_2$ (60 mL) was heated to reflux overnight. The mixture was concentrated in vacuo. The residue was dissolved with toluene (30 mL), and concentrated in vacuo to give the crude product, which was used for the next step directly.

Step 2: Preparation of Compound 3

To a boiled solution of crude compound 2 (42 mmol) in toluene (100 mL) was added a suspension of aniline (6.17 g, 42 mmol) in toluene (40 mL) slowly, and refluxed for 2 h. The mixture was concentrated in vacuo to give a solid, which was used for the next step directly.

Step 3: Preparation of Compound (1)

To a solution of compound 3 (42 mmol) in MeCN (250 mL) was added amine 4 (4.3 g, 42 mmol) and Et$_3$N (6.18 g, 61.2 mmol) at rt, and the mixture was stirred at room temperature for 3 h. The solution was concentrated in vacuo. The residue was purified by silica gel chromatography to give the desired product as white solid (15.7 g, 86.5%). H-NMR (Methanol-d4 400 MHz): 8.41-8.39 (dd, J=6.5, 2.4 Hz, 1H), 8.26-8.23 (m, 1H), 7.61-7.50 (m, 3H), 3.74-3.72 (m, 1H), 3.56-3.52 (m, 2H), 3.06-3.01 (m, 2H), 1.91-1.87 (m, 2H), 1.59-1.56 (m, 2H). LCMS: 433.0 [M+1].

II. Alternative Synthesis

Step 1: Preparation of Compound 2: Step 1 of the method described in Section I of this Example (preparation of compound 2) can be carried out in the presence of about 2-3 equivalents of SOCl$_2$, rather than utilizing SOCl$_2$ as a solvent. This modification (reducing the amount of SOCl$_2$) is advantageous for safety reasons: at larger production scales, the reaction could generate significant gas release and react violently in an instance of contact with water.

In 1 L reactor under moderate mechanical agitation and under Nitrogen are loaded: 200 mL (4 vol) of toluene; 50.02 g of 3-chlorosulfonyl-4-fluorobenzoic acid (containing 8% w/w (50% mol) of water); and 200 mL (4 vol) of toluene to rinse. The temperature is maintained at 25° C. and 14.1 mL (1 eq) of SOCl$_2$ is added. This is a slightly exothermic reaction with light gassing (SO$_2$+HCl). At the end of the addition, the suspension is stirred for 20 minutes at 25° C. and then heated to reflux. Gassing becomes more important to 35-40° C. and the mixture starts to foam. The starting acid is dissolved at 80° C. The mixture is then a pale yellow solution with some brown particles in suspension. Gassing and foam decrease from 90-100° C.

When reflux is reached: a solution of 0.740 mL in 100 mL of DMF (2 vol.) toluene is quickly added, then in 30 min, 18.3 mL (1.3 eq) of SOCl$_2$. The yellow solution is stirred under reflux for 2 h 50 min (end of gassing after 2 hours) 96.8% conversion was observed according to the HPLC Conditions provided below. The toluene is reduced by distillation to 3 volumes. 250 mL (5 vol) of toluene are added and distilled again to 3 volumes. The solution is then cooled to 25° C. and left under stirring overnight.

HPLC Conditions:
Column: Inertsil ODS-3 15×0.46 cm×3 μm
Wave length (nm): 260
Flow (mL/min): 1.0
Oven (° C.): 30
Injection (μL): 10
Phase A: CH$_3$COONH$_4$ 0.01M
Phase B: ACN
Gradient:

| Times (min) | A (%) | B (%) |
|---|---|---|
| 0-1 | 90 | 10 |
| 20-25 | 10 | 90 |
| 26-35 | 90 | 10 |

Dissolution Solvent: CH$_3$CN
Concentration: 0.5 mg/ml

To 50 μl of mixture 100 μl of MeOH are added. The solution is heated at 100° C. 1 to 2 min and 10 ml of CH$_3$CN are added Step 2: Preparation of Compound 3: 350 mL (7 vol) of toluene are added to the above yellow-orange solution, which is then heated to reflux. Once the solution is refluxing, 28.37 g of trifluoroaniline in 150 mL (3 vol) of toluene (+50 mL (1 vol) of toluene for rinsing) are added in 40 minutes. The brown solution is stirred under reflux for 2 h 30 min. The conversion was observed at 99.7% according to the HPLC method described above in Step 1. The mixture is cooled at 15° C. in 40 min. and maintained at 15° C. for 1 h 30. The obtained suspension is filtered and washed with 150 mL of toluene. The solid is then dried in a vacuum oven at 50° C. for 3 days.

Step 3: Preparation of Compound (1): Step 3 of the method described in Section I of this Example can be carried out with acetone as the solvent, rather than acetonitrile. Using acetone as the solvent results in Form III of Compound (1) as follows:

In a 1 L reactor under moderate mechanical stirring (160 r/min) at 20° C. are introduced: 40 g of compound 3; 11 g (1 eq) of 4-hydroxypiperidine; and 280 mL (7 vol) of acetone. The mixture is heated to 45° C. and 18.2 mL (1.2 eq) of triethylamine are added in 15 min. The solution is stirred at 45° C. for 1 h 30 min. The conversion is observed at 100.0% (same HPLC conditions as described in Step 1, however the sample is prepared only in CH$_3$CN without MeOH). 122 mL (3 vol) of water are quickly added to the mixture at 45° C. resulting in total dissolution of salts. The hot solution is filtered and reintroduced in the reactor. 60 mL (1.5 vol) of acetone is used to rinse the reactor and the filter. The mixture is cooled to 35° C. and 225 ml of water are added in 40 min. The temperature is then cooled to from 35 to 10° C. in 20 min. and maintained at 10° C. overnight under vigorous stirring. The suspension is filtered and washed with 2×120 ml (2×3 vol) of acetone/H$_2$O (50/50).

The solid is dried in a ventilated oven at 45° C. overnight. 43.6 g (86% yield) of Compound (1) are obtained.

Figure 13A:
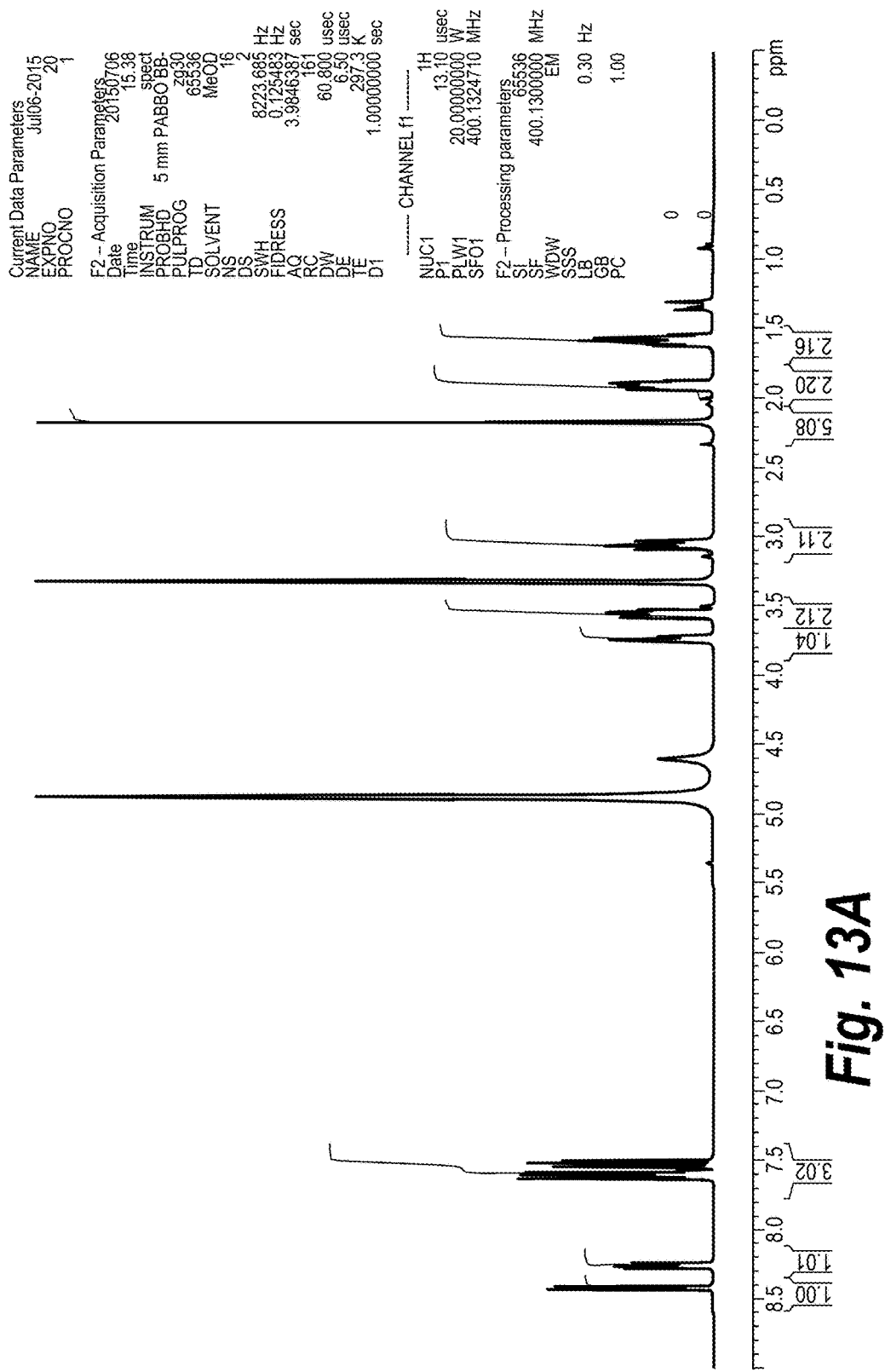
FIG. 13A shows the $^1$H NMR spectrum of Form III in MeOD.
Figure 13B:
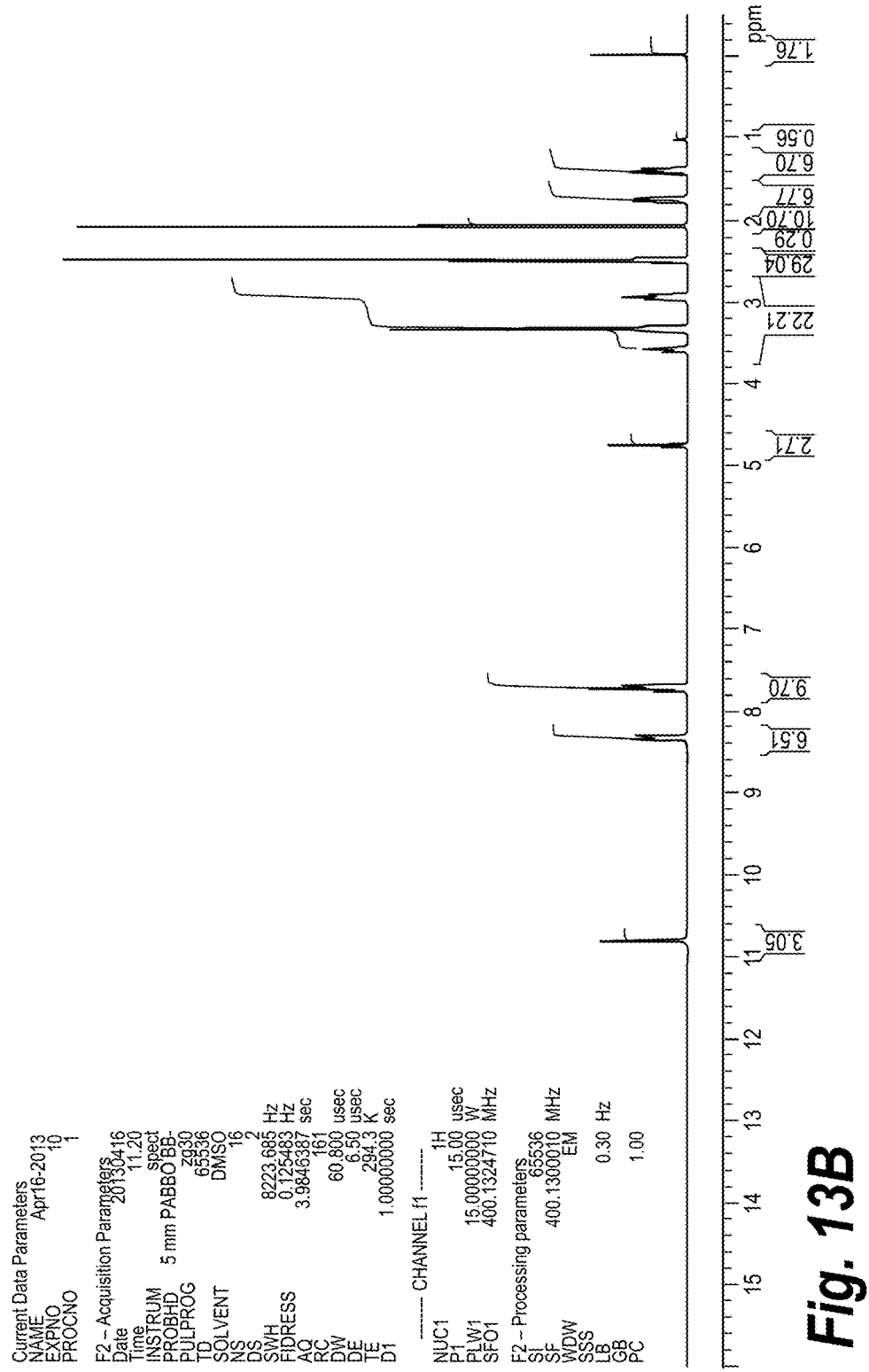
FIG. 13B shows the $^1$H NMR spectrum of Form III in DMSO-d6.

The $^1$H NMR analysis of Form III is shown in FIGS. 13A and 13B. The XRPD confirmed the acetone form (i.e., Form III).

Example 2

Anhydrous Form I of Compound (1)

I. Process for the Formation of Anhydrous Form I of Compound (1)

The following process was developed for the production of Form I of Compound (1).

Acetone (5.3 V) was added to compound (1) at 45° C. Water was then added, and the solution was filtered at 45° C. to remove mechanical impurities. The solution was then cooled to 20° C. and water (2.5 V) was poured in as quickly as possible. Caking occurred during this process, i.e., crystallization of the acetone form. The solution was cooled further to 10° C., consuming supersaturation. A slurry was then formed with 3V of a mixture of acetone and water (50/50) at 10° C., followed by washing with a solution of the same. Filtration and drying at about 50° C. under vacuum resulted in Form III of Compound (1).

A slurry was formed from mixing the resulting Form III of Compound (1) with methyl tert-butyl ether (MTBE) at 25° C. over at least 4 hours. This step produced an anhydrous phase, which was dried on a filter-dryer at 30° C. under nitrogen while alternately stirring. This resulted in "anhydrous" Form I of Compound (1) (wherein the solvent content is in compliance with ICH standard). Manual milling and sieving (on 1 mm grid) resulted in a powder composed of fine particles (below 25 μm) for a total yield of about 79%.

This crystallization processes allowed for the production of approximately 600 g of anhydrous Compound (1) of Form I of satisfactory purity (99.6% with no individual impurity higher than 0.20%). The purity of Compound (1) can be determined by the following HPLC conditions:

| Column: | Inertsil ODS-3 3 μm, 150 × 4.6 mm or equivalent |
|---|---|
| Wave-length (nm): | 235 |
| Flow rate (ml/min): | 1.0 |
| Temperature (° C.): | 20 |
| Injection volume (μl): | 7 |
| Analysis time (min): | 40 |
| Mobile Phase: | A: KH$_2$PO$_4$ 0.01, pH 3.0 (H$_3$PO$_4$) |
| | B: CH$_3$CN |
| | C: Methanol |

Gradient:

| Time (min) | % A | % B | % C |
|---|---|---|---|
| 0 | 50 | 40 | 10 |
| 19 | 20 | 70 | 10 |
| 29 | 20 | 70 | 10 |
| 30 | 50 | 40 | 10 |
| 40 | 50 | 40 | 10 |

| Dissolution solvent and diluent: | CH$_3$CN |
|---|---|
| Nominal concentration (mg/mL): | 0.5 |

II. Characterization of Form I of Compound (1)

A representative X-ray powder diffraction pattern of Form I is shown in FIG. 1. Table 1 also shows XRPD data for a sample of Form I of Compound (1).

TABLE 1

X-Ray powder diffraction pattern of Compound (1) (Form I Mixture of anhydrous phases)

| No. | Pos. [°2-theta] | Height [cts] |
|---|---|---|
| 1 | 3.6236 | 617 |
| 2 | 6.3326 | 265.66 |
| 3 | 7.1217 | 138.28 |
| 4 | 7.8715 | 533.79 |
| 5 | 8.2138 | 432.54 |
| 6 | 10.655 | 598.62 |
| 7 | 11.9888 | 369.67 |
| 8 | 12.6413 | 328.43 |
| 9 | 13.6496 | 464.63 |
| 10 | 14.1037 | 1257.15 |
| 11 | 14.7109 | 361.68 |
| 12 | 15.5809 | 472.99 |
| 13 | 16.2387 | 617.25 |
| 14 | 16.7991 | 1255.46 |
| 15 | 17.9967 | 1408.24 |
| 16 | 18.3098 | 1380.51 |
| 17 | 19.1598 | 899.96 |
| 18 | 19.8137 | 985.25 |
| 19 | 20.5019 | 2706.84 |
| 20 | 21.114 | 801.08 |
| 21 | 21.9466 | 1245.18 |
| 22 | 23.1552 | 882.81 |
| 23 | 24.6748 | 1796.11 |
| 24 | 25.8704 | 461.03 |
| 25 | 26.3304 | 1551.01 |
| 26 | 27.3986 | 525.64 |
| 27 | 29.598 | 343.14 |
| 28 | 30.2827 | 264.97 |
| 29 | 31.7769 | 198.8 |
| 30 | 34.5028 | 200.08 |
| 31 | 36.1957 | 230.18 |
| 32 | 38.1977 | 113.97 |
| 33 | 41.5299 | 57.49 |

Form I of Compound (1) was further characterized by TGA, DSC, and DVS. A description of this characterization is found in Example 5.

Example 3

Formation and Characterization of an Anhydrous Crystalline Form of Compound (1) (Form XVI)

I. Process for the Formation of Form XVI of Compound (1)

Acetone (7V) was added to Compound (1) at 45° C. Water (3V) was added, and the solution was filtered to remove mechanical impurities. The solution was then cooled to 20° C., and the solution was seeded with 0.7% of Form III of Compound (1) to form Form III. Additional water (4 V) was added to achieve a 50/50 acetone to water ratio. The solution was then cooled to 10° C. over 20 min, consuming supersaturation. A slurry was then formed with 4V of a mixture of acetone and water (50/50) at 10° C., followed by washing with a solution of the same. Filtration and drying at about 50° C. under nitrogen saturated with acetone resulted in Form III of Compound (1). Further Filtration and drying at about 50° C. under nitrogen resulted in "dried" Form III of Compound (1).

A slurry was formed from mixing the resulting dried Form III of Compound (1) with methyl tert-butyl ether (MTBE, 4V) at about 20° C. over at least 2 hours. The led to the transition from Form III to the anhydrous forms of Compound (1), Form I and Form XVI. The resulting forms were washed with MTBE (3V) at about 20° C., and then dried on filter-dryer at 70° C. under nitrogen with stirring, resulting in "anhydrous" Form XVI of Compound (1), (wherein the solvent content is in compliance with ICH standard).

This process led to the intended anhydrous crystalline form, Form XVI, of Compound (1) with a satisfactory purity: 99.4% with a particular impurity, below 0.20%. The particular impurity level was decreased from approx. 7% to less than 0.20% by the re-crystallization and MTBE slurry. The yield was about 75%. The purity of Compound (1) can be determined by the HPLC method described in Example 2, Section I.

II. Alternative Process for the Formation of Form XVI of Compound (1)

Alternatively, Form XVI of Compound (1) can be made by the following process.

Compound (1) is dissolved by addition of acetone (6.5V) at 45° C. followed by 3V of water. The solution was then filtered to remove mechanical impurities. Acetone was added to rinse the lines. The solution was then cooled to 20° C. and seeded with 0.1% of Form III of Compound (1). Water (4V) was added and the solution was cooled to 10° C. The solution was then stirred over at least 2 hours. The solution was then filtered under nitrogen at 10° C. A slurry was formed at 10° C. in a mixture of acetone and water (4V, 50/50 V/V). The resulting solids were washed twice with a mixture of acetone and water (3V, 50/50 V/V). The resulting wet cake was then dried under nitrogen with stirring until the weight loss becomes inferior to 4% (measured by TGA analysis). This product was cooled to 10° C., and transitioned to Form III of Compound (1) by exposure to nitrogen saturated in acetone until loss in weight is inferior to 10% (by TGA analysis). The resulting product was the dried acetone form (Form III of Compound (1)).

A slurry was formed from mixing the resulting dried Form III of Compound (1) with methyl tert-butyl ether (MTBE, 4V) at about 20° C. during at least 2 hours. The resulting product was washed with MTBE (3V) at about 20° C., and then dried at 50° C. to yield Form XVI of Compound (1). The final product was milled and sieved on a 1 mm grid.

III. Characterization of Form III of Compound (1)

The X-ray powder diffraction pattern of Form III is shown in FIG. 4. Table 2 also shows XRPD data for a sample of Form III of Compound (1).

TABLE 2

X-Ray powder diffraction pattern of Compound (1)
(Form III, Solvate of Acetone)

| No. | Pos. [°2-theta] | Height [cts] |
|---|---|---|
| 1 | 6.1533 | 339.26 |
| 2 | 9.0816 | 1104.7 |
| 3 | 9.9483 | 1907.02 |
| 4 | 10.0321 | 1552.49 |
| 5 | 12.1685 | 3556.97 |
| 6 | 12.9616 | 383.96 |
| 7 | 14.2397 | 315.01 |
| 8 | 15.1483 | 2480.83 |
| 9 | 16.2048 | 1828.9 |
| 10 | 16.8775 | 256.66 |
| 11 | 18.269 | 953.62 |
| 12 | 18.6378 | 3776.85 |
| 13 | 19.9348 | 205.82 |
| 14 | 21.1993 | 1960.44 |
| 15 | 21.9332 | 550.39 |
| 16 | 22.2455 | 479.41 |
| 17 | 23.1308 | 548.36 |
| 18 | 24.4803 | 948.12 |
| 19 | 25.4636 | 170.21 |
| 20 | 25.8397 | 586.56 |
| 21 | 26.139 | 787.4 |
| 22 | 26.7489 | 173.31 |
| 23 | 27.404 | 149.44 |
| 24 | 28.053 | 307.13 |
| 25 | 28.9464 | 155.2 |
| 26 | 30.0145 | 564.17 |
| 27 | 31.9986 | 284.25 |
| 28 | 33.0882 | 659.21 |
| 29 | 34.0244 | 203.24 |
| 30 | 34.3991 | 227.63 |
| 31 | 37.0076 | 210.03 |
| 32 | 38.3419 | 102.07 |
| 33 | 40.4682 | 165.35 |
| 34 | 42.4278 | 144.39 |

Figure 5:
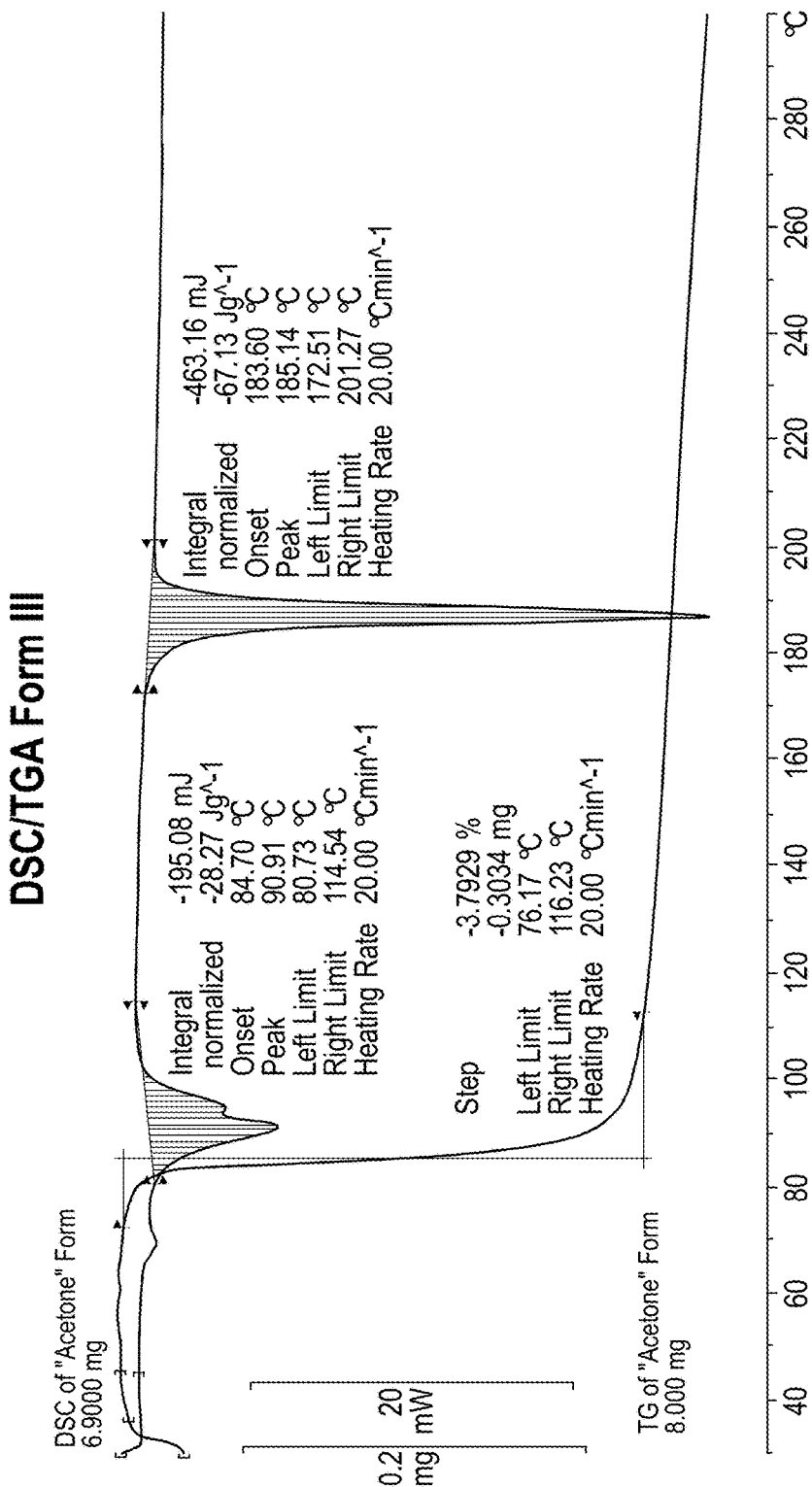
FIG. 5 shows the thermogravimetry (TGA) curve and the differential scanning calorimetry (DSC) curve of Form III.

Form III was analyzed by DSC and TGA (FIG. 5). The first melting point (starting around 80° C.) is accompanied by weight loss (3.8%). This is consistent with a solvated form.

IV. Characterization of Form XVI of Compound (1)

The X-ray powder diffraction pattern of Form XVI is shown in FIG. 8. Table 3 also shows XRPD data for a sample of Form XVI of Compound (1).

TABLE 3

X-Ray powder diffraction pattern of Compound (1) of Form XVI

| No. | Pos. [°2-theta] | Peak Height [cts] |
|---|---|---|
| 1 | 8.3325 | 177.19 |
| 2 | 10.9344 | 1935.52 |
| 3 | 14.3722 | 3710.48 |
| 4 | 14.9241 | 373.24 |
| 5 | 15.8427 | 2224.43 |
| 6 | 16.4561 | 2064.13 |
| 7 | 17.0677 | 5116.86 |
| 8 | 18.5296 | 4972.27 |
| 9 | 18.9049 | 872.76 |
| 10 | 20.0163 | 3381.98 |
| 11 | 20.7658 | 13446.21 |
| 12 | 21.5994 | 1648.19 |
| 13 | 22.1592 | 5552.43 |
| 14 | 22.8341 | 878.36 |
| 15 | 23.4421 | 2910.94 |
| 16 | 23.6338 | 2169.37 |
| 17 | 24.9292 | 12671.51 |
| 18 | 26.5972 | 15673.37 |
| 19 | 27.9963 | 3230.31 |
| 20 | 28.3825 | 1934.34 |
| 21 | 29.5627 | 1788.4 |
| 22 | 29.766 | 1697.44 |
| 23 | 30.4527 | 1526.62 |
| 24 | 31.1958 | 954.79 |
| 25 | 31.7034 | 1030.38 |
| 26 | 32.9259 | 1755.93 |
| 27 | 34.1563 | 1312 |
| 28 | 34.5404 | 2059.7 |
| 29 | 35.6022 | 1008.97 |
| 30 | 36.3734 | 2480.94 |
| 31 | 36.753 | 1575.29 |
| 32 | 38.3689 | 1684.63 |
| 33 | 39.7099 | 915.35 |
| 34 | 40.1675 | 1190.9 |
| 35 | 41.707 | 685.21 |
| 36 | 43.6419 | 800.32 |
| 37 | 44.6892 | 1534.39 |

Form XVI of Compound (1) was further characterized by TGA, DSC, and DVS. A description is found below in Example 5.

Example 4

Hydrate Crystalline Form of Compound (1) (Form XII)

Certain steps in the process during the scale-up in production led to the isolation of the hydrate form of Compound (1), Form XII. The X-ray powder diffraction pattern of Form XII is shown in FIG. 6. Table 4 also shows XRPD data for a sample of Form XII of Compound (1).

TABLE 4

X-Ray powder diffraction pattern of Compound (1) (Form XII Hydrate)

| No. | Pos. [°2-theta] | Height [cts] |
|---|---|---|
| 1 | 8.0541 | 375.88 |
| 2 | 10.9322 | 2002.44 |
| 3 | 12.8521 | 645.35 |
| 4 | 13.3741 | 1407.49 |
| 5 | 14.1334 | 1341.07 |
| 6 | 14.8304 | 1311.02 |
| 7 | 15.0968 | 1958.7 |
| 8 | 15.3488 | 1417.84 |
| 9 | 15.6213 | 3745.9 |
| 10 | 16.0829 | 4106.81 |
| 11 | 17.1472 | 1740.33 |
| 12 | 18.3148 | 742.51 |
| 13 | 19.1022 | 492.08 |
| 14 | 19.6178 | 1161.9 |
| 15 | 20.8517 | 2768.7 |
| 16 | 21.4251 | 601.43 |
| 17 | 22.0905 | 1464.16 |
| 18 | 23.7739 | 1342.99 |
| 19 | 24.1035 | 859.78 |
| 20 | 24.4825 | 922.56 |
| 21 | 24.9045 | 5552.81 |
| 22 | 24.9487 | 5688.78 |
| 23 | 26.0631 | 904.91 |
| 24 | 26.8877 | 1801.55 |
| 25 | 27.2243 | 4791.14 |
| 26 | 28.1029 | 756.53 |
| 27 | 28.81 | 355.08 |
| 28 | 29.4999 | 713.41 |
| 29 | 29.8122 | 416.46 |
| 30 | 30.1148 | 429.55 |
| 31 | 30.9143 | 277.83 |
| 32 | 31.4202 | 1315.56 |
| 33 | 32.013 | 799.53 |
| 34 | 33.2694 | 386.22 |
| 35 | 33.7561 | 454.97 |
| 36 | 34.0586 | 856.13 |
| 37 | 34.6778 | 463.2 |
| 38 | 35.1602 | 378.03 |
| 39 | 36.1419 | 236.02 |
| 40 | 37.6653 | 554.87 |
| 41 | 39.1029 | 311.06 |
| 42 | 39.6124 | 359.12 |
| 43 | 40.9976 | 318.22 |
| 44 | 41.5859 | 112.96 |
| 45 | 42.502 | 136.78 |

Figure 7:
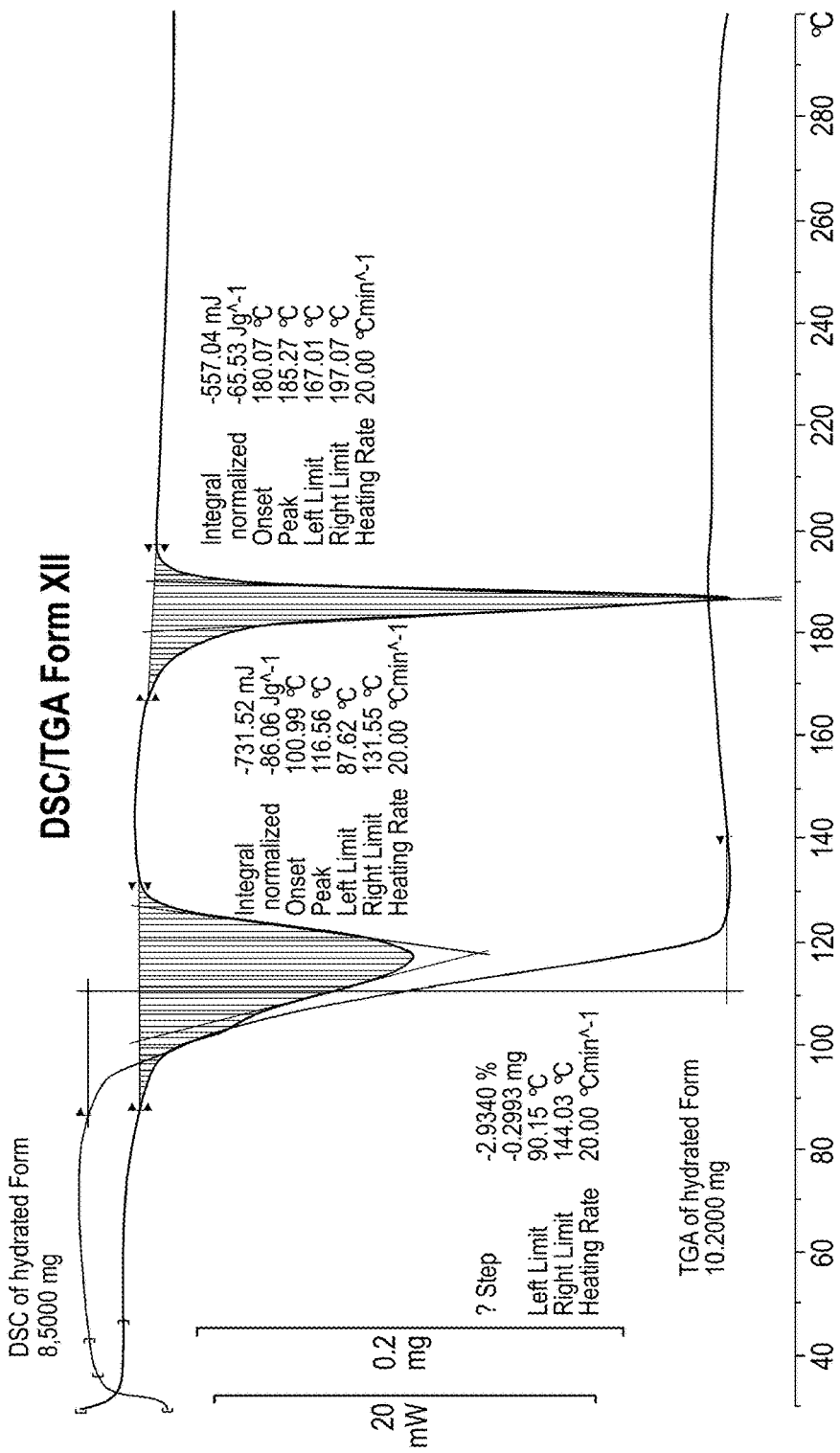
FIG. 7 shows the thermogravimetry (TGA) curve and the differential scanning calorimetry (DSC) curve of Form XII.

Form XII of Compound (1) was analyzed by DSC and TGA (FIG. 7). The first melting point is around 100° C. and a loss of weight (3%) is concomitantly observed. This confirms the presence of a hydrated form.

Example 5

Comparison and Characterization of Anhydrous Forms of the Compound of Formula (1)

Samples of Form I and Form XVI were characterized and compared. A summary of this comparison is found in Table 5. The samples were further characterized by optical microscopy and SEM. Form I presents itself as an off-white powder, and exhibits a plate habit with the presence of agglomerates and very fine particles which suggests a polymodal particle size distribution. Form XVI presents itself as an off-white powder and exhibits a plate habit with mainly very fines particles and a few agglomerates.

TABLE 5

Comparison of Properties Between Forms I and XVI of Compound (1)

| | FI | FXVI |
|---|---|---|
| Habit | Platelets<br>Small particles and some agglomerates. | Platelets<br>Small particles and some agglomerates. |
| Solubility | In Water <2 g/L at 25° C.<br>In MTBE <2 g/L at 25° C. | In Water <2 g/L at 25° C.<br>In MTBE <2 g/L at 25° C. |
| pH solubility profile | Slightly soluble | Slightly soluble |
| DSC/TGA/Hotstage | First melting point: 143° C.<br>Second melting point: 185° C. (enthalpy of −71 J/g)<br>Decomposition >300° C. | Melting point: 185° C.<br>With enthalpy of −74 J/g<br>Decomposition >300° C. |
| Hygroscopicity (DVS, 37° C.) | Uptake of 1.5% from 0 to 100% ◊ slightly hydrophilic. No hysteresis | Uptake of 0.8% from 0 to 100% ◊ slightly hydrophilic. No hysteresis |
| Particle Size Distribution (PSD) after sonication | D10 = 4.7 μm<br>D50 = 14.2 μm<br>D90 = 66.9 μm<br>Weakly bound agglomerates | D10 = 4.2 μm<br>D50 = 20.0 μm<br>D90 = 37.5 μm<br>Weakly bound agglomerates |
| XRPD under temperature | Complete transition towards FXVI at 160° C. | No transition phase until 160° C. |
| XRPD under RH | No transition phase from 10% to 80% RH at 25° C. | No transition phase from 10% to 80% RH at 25° C. |

The XRPD pattern of Form I is shown in FIG. 1. The XRPD pattern of Form XVI is shown in FIG. 8.

Thermal Analysis

Figure 2:
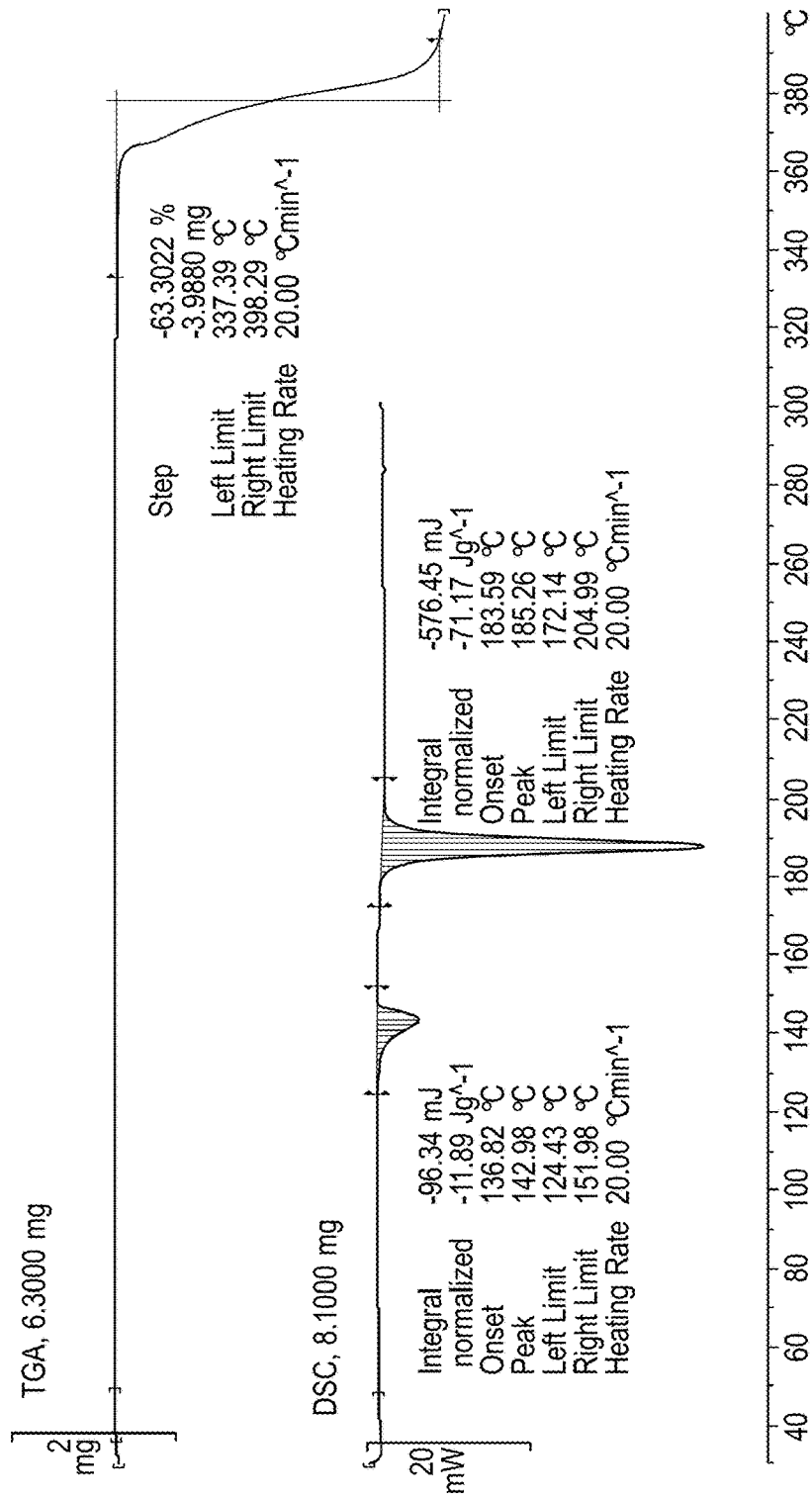
FIG. 2 shows the thermogravimetry (TGA) curve (upper) and the differential scanning calorimetry (DSC) curve (lower) of Form I.
Figure 3:
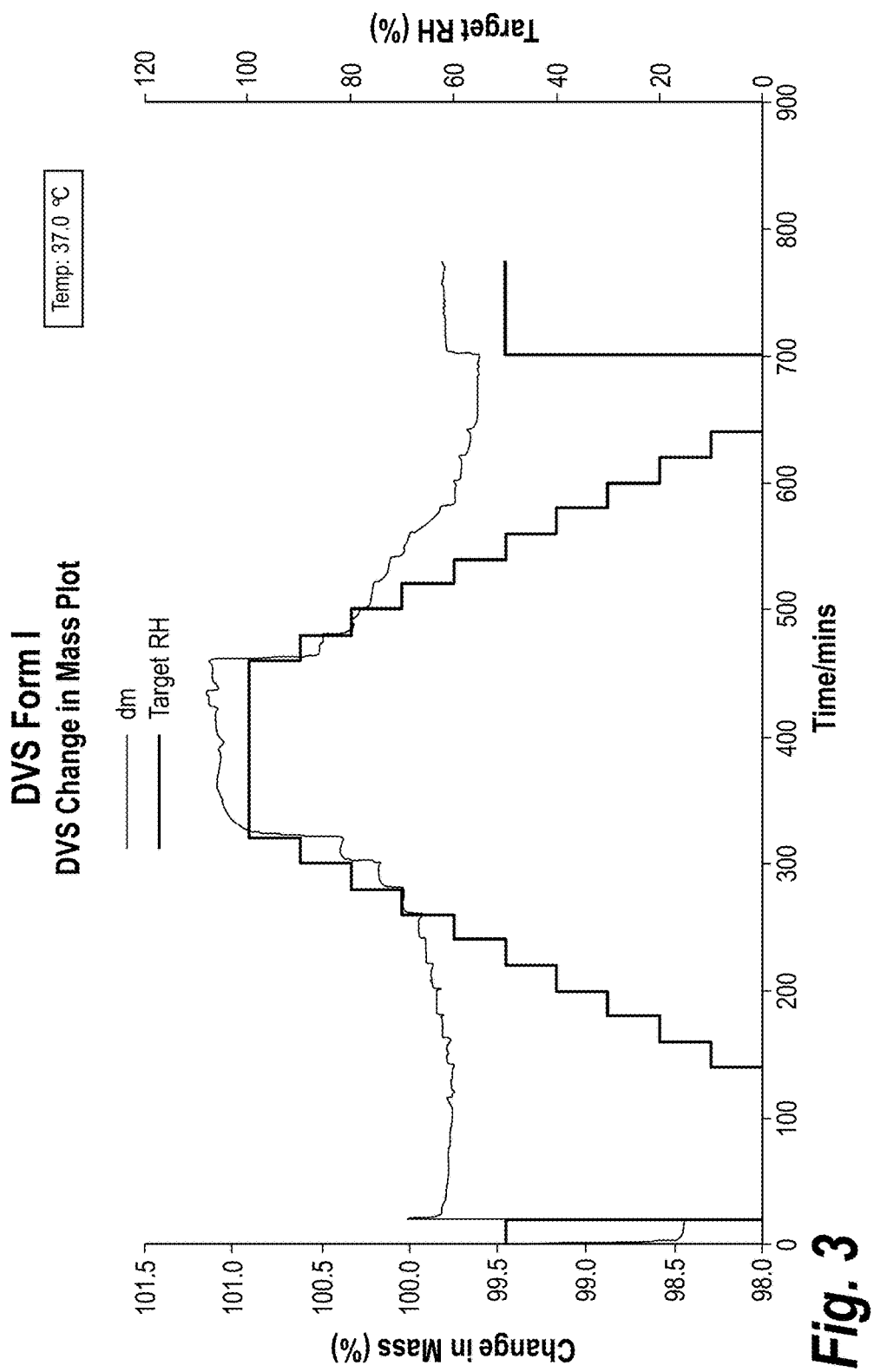
FIG. 3 shows the DVS graph of Form I.

The thermal analysis of Form I is shown in FIG. 2. The DSC experiments show a melting point at 143° C. following directly by recrystallization (concomitant phenomena). A second endothermic peak occurs at 185° C. with an enthalpy of energy of −71 J/g. The TGA confirmed the presence of an anhydrous compound with no loss in weight during the melting point. The degradation occurs above 300° C.

Figure 9:
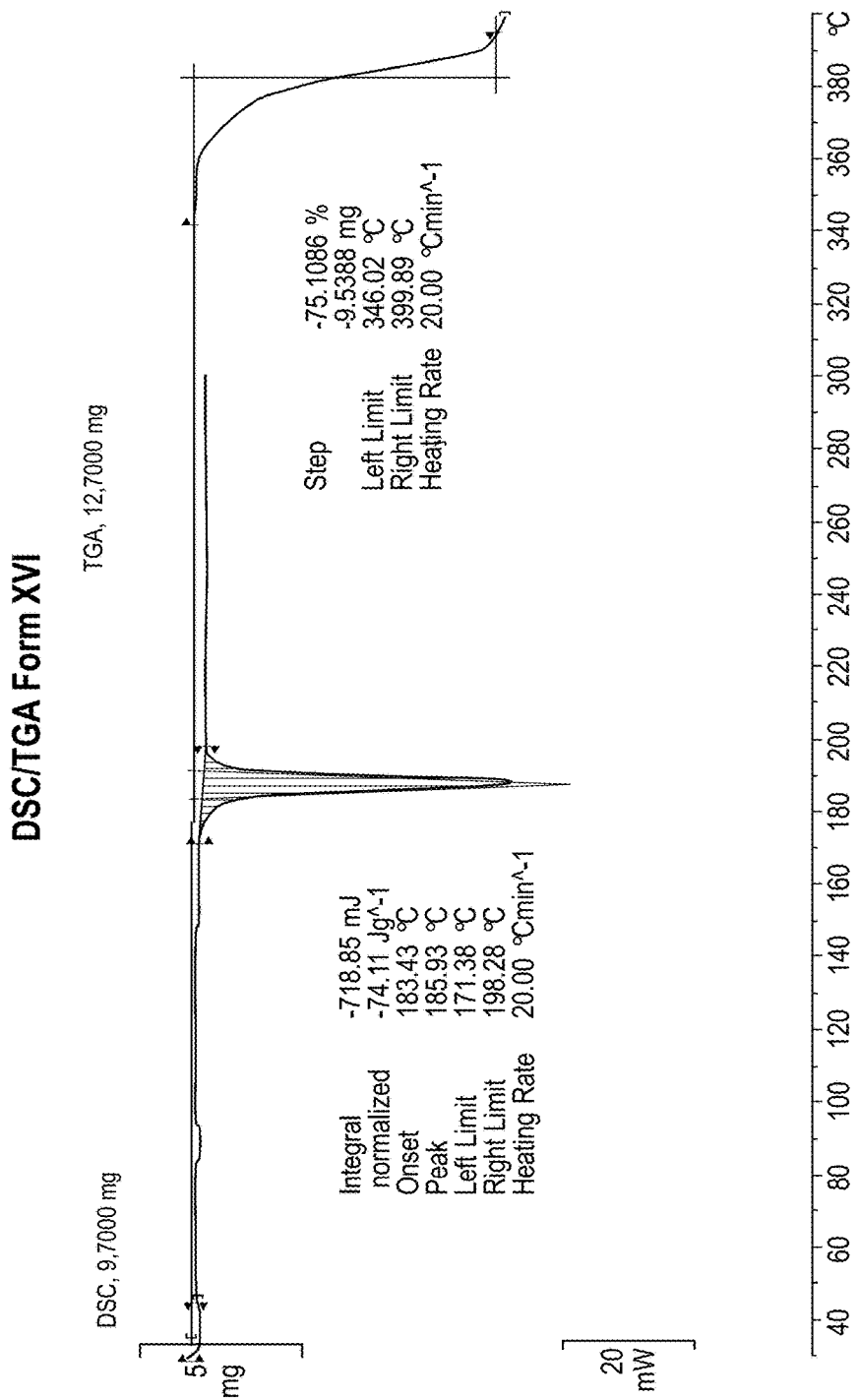
FIG. 9 shows the thermogravimetry (TGA) curve and the differential scanning calorimetry (DSC) curve of Form XVI.

The thermal analysis of Form XVI is shown in FIG. 9. The DSC experiments show a pure crystalline form with a melting point at 185° C. with an enthalpy of energy of −74 J/g. It corresponds to the second melting point observed on Form I. The TGA analysis confirms the presence of an anhydrous compound with no loss in weight during the melting point. The degradation occurs above 300° C.

DVS

The DVS measurements of Form I show a water uptake of 1.5% from 0% to 100% RH at 37° C. This crystalline form can be considered slightly hydrophilic. No hysteresis is observed between the initial and final state (see FIG. 3).

The DVS measurements of Form XVI show a water uptake of 0.8% from 0% to 100% RH at 37° C. This crystalline can be considered slightly hydrophilic. No hysteresis is observed between the initial and final state (see FIG. 10).

Stability Under Simulated Storage Conditions: XRPD

The stability of crystalline Forms I and XVI was characterized by XRPD under temperature and relative humidity conditions that stimulate potential storage conditions.

Figure 11A:
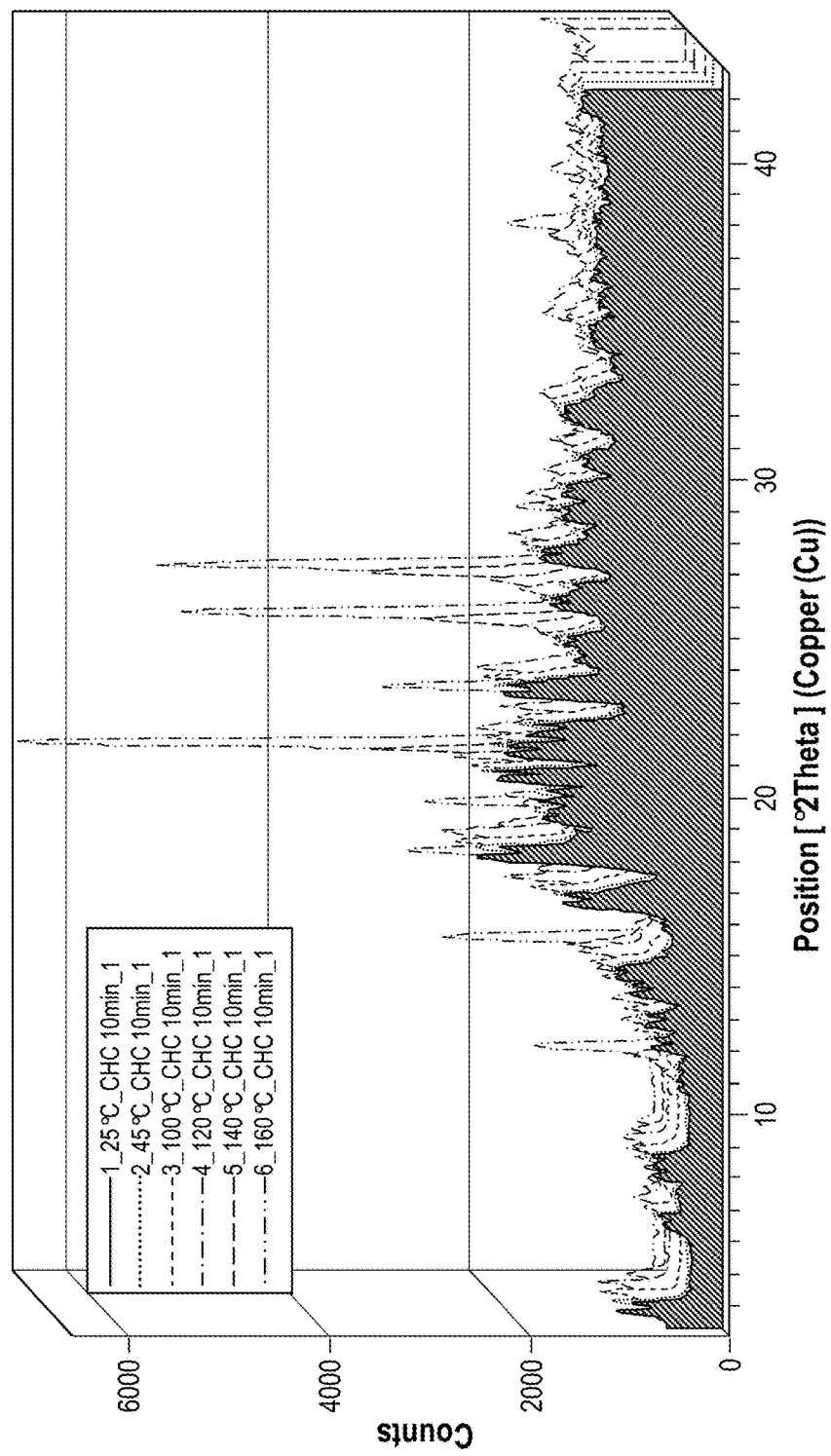
FIG. 11A shows the X-ray powder diffraction patterns of Form I over the course of a stability study upon increasing the temperature from 25° C. (first, front pattern) to 160° C.
Figure 11B:
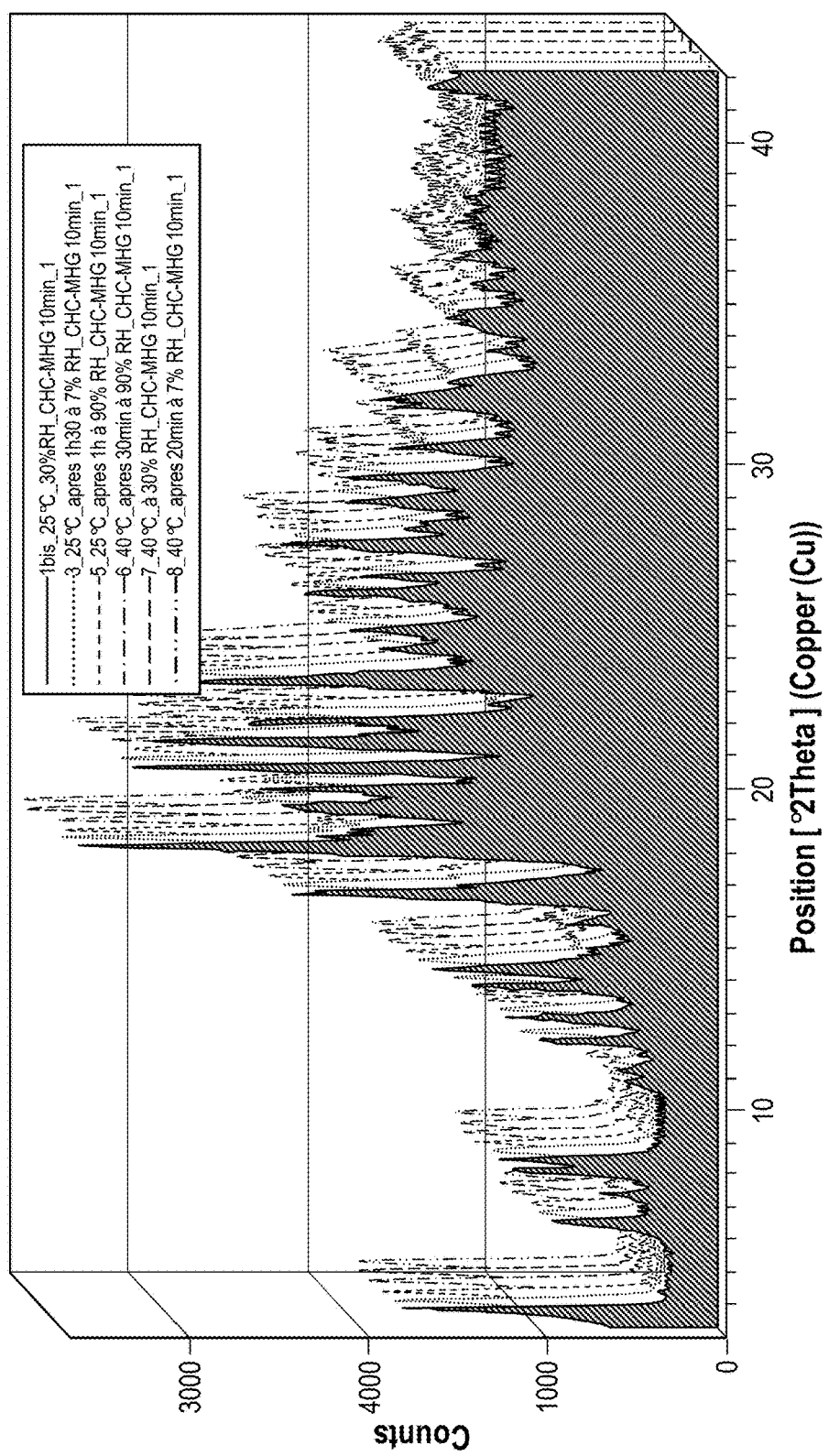
FIG. 11B shows the X-ray powder diffraction patterns of Form I as subjected to varying levels of humidity (7%, 30%, and 90%) at two different temperatures (25° C. and 40° C.).

XRPD analysis shows that Form I is sensitive to the temperature with a phase transition from 100° C. and is complete at 160° C. (FIG. 11A). It should be noticed that this phase transition is not reversible. The RH has no impact on the crystalline phase within the range of relative humidity (7-30-90%) either at 25 or 40° C. (FIG. 11B).

Figure 12A:
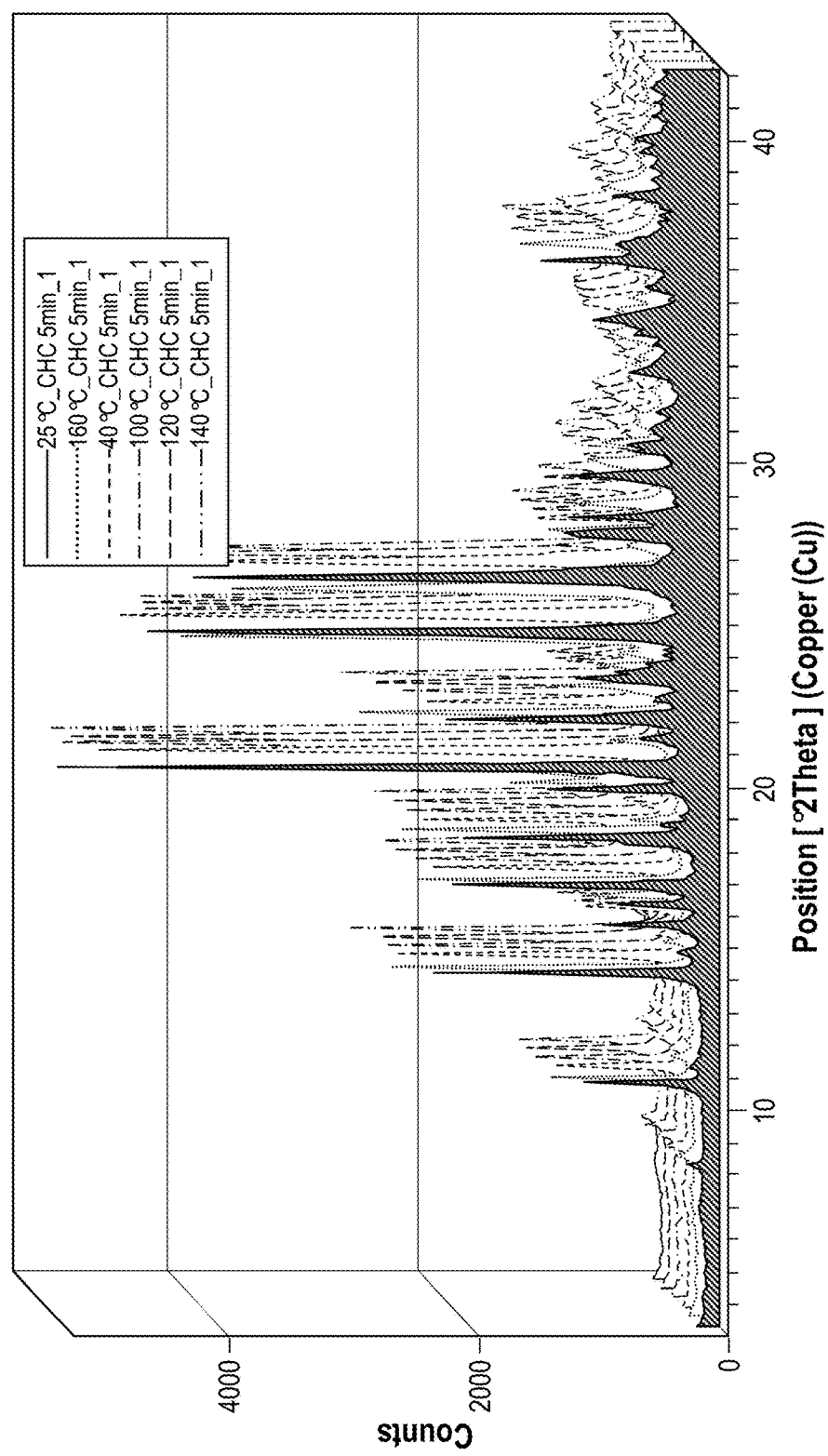
FIG. 12A shows the X-ray powder diffraction patterns of Form XVI over the course of a stability study upon increasing the temperature from 25° C. (first, front pattern) to 160° C. (last, back pattern).
Figure 12B:
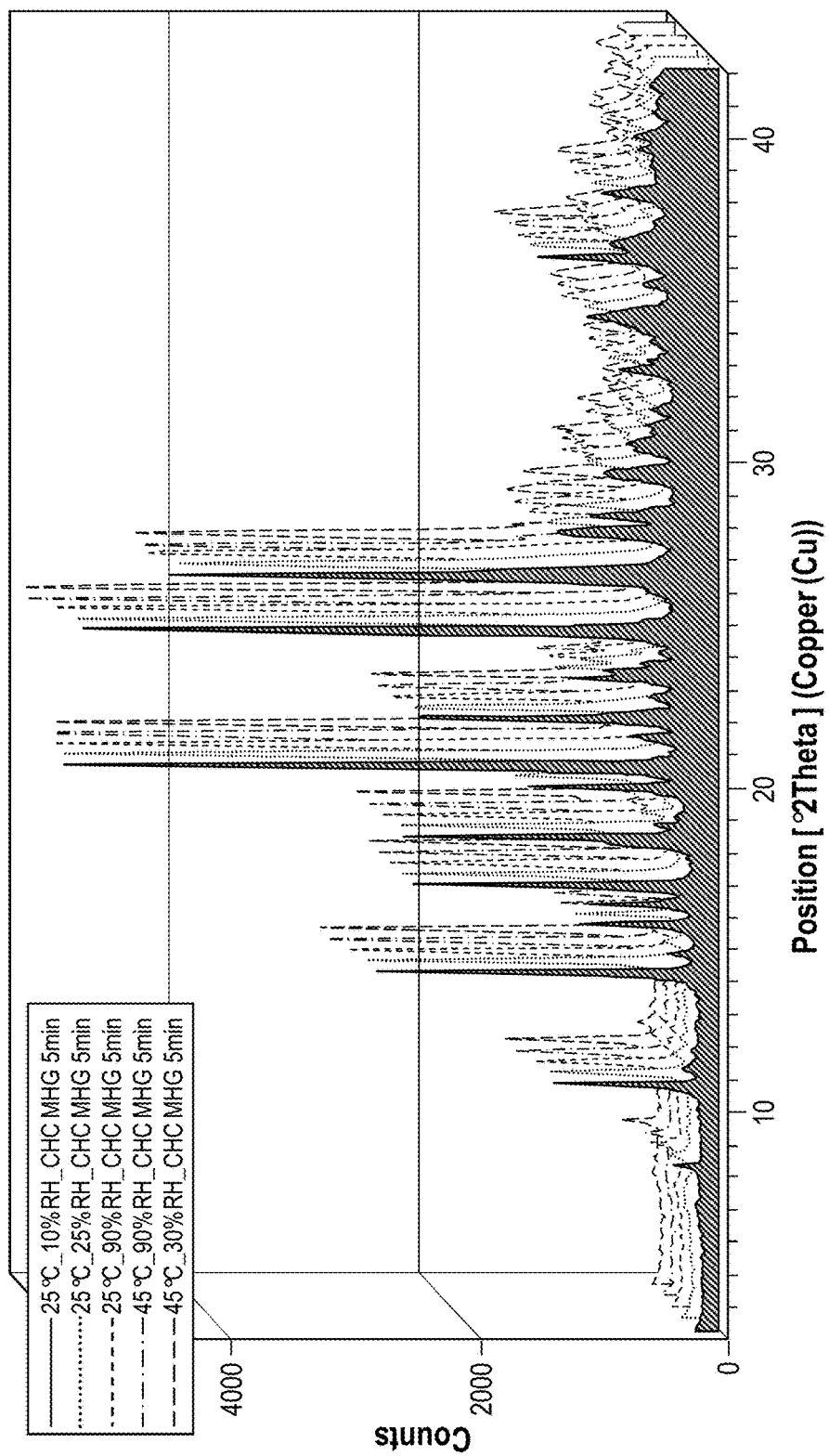
FIG. 12B shows the X-ray powder diffraction patterns of Form XVI as subjected to varying levels of humidity (e.g., 10%, 25%, 30%, and 90%) at two different temperatures (25° C. and 45° C.).

XRPD analysis shows that Form XVI undergoes no phase transition when temperature is increased from 25° C. to 160° C. (FIG. 12A). Relative Humidity has no impact on the crystalline phase within the range 7-30-90% either at 25 or 45° C. (FIG. 12B). This behavior indicates a high stability of this anhydrous form with respect to temperature and relative humidity, which is important for further development and especially for withstanding variable storage conditions.

Particle Size Distribution

Form I: The volumetric measurements obtained were D10=5.8 µm, D50=69.1 µm and D90=342.6 µm. From these results, the distribution is polymodal (bimodal) which is confirmed by optical microscopy. There are some fines particles (<10 µm) and another population composed of larger particles (>100 µm). These agglomerates are composed of fines particles (primary particles) and it is expected that the degree of agglomeration is weak. This can be confirmed by laser diffraction with ultrasound treatment. The volumetric diameter obtained are D10=4.7 µm, D50=14.2 µm and D90=66.9 µm. The analyses after ultrasound treatment confirm that the agglomerates are composed of primary particles. A sonication period of 40 seconds was employed to remove the agglomeration without affecting the primary particles. After comparison of these Malvern analyses, it can be concluded that the powder consists of weakly bound agglomerates that can be broken by weak shearing, as applied during the formulation processes.

Form XVI: The volumetric diameter obtained are D10=9.8 µm, D50=23.7 µm and D90=45.8 µm. From these results, the distribution is polymodal (bimodal) which is confirmed by optical microscopy. There is a main population (<30 µm) and some agglomerates (>100 µm). These agglomerates are composed of fines particles (primary particles). It is expected that the degree of agglomeration is weak. This was confirmed by laser diffraction with ultrasound treatment. The volumetric diameter obtained are D10=4.2 µm, D50=20.0 µm and D90=37.5 µm. The analyses, after ultrasound treatment, confirm that any agglomerates present comprise primary particles. A sonication period of 40 seconds was employed in order to remove the agglomeration without affecting the primary particles. After comparison of these Malvern analyzes, it can be concluded that the powder consists of weakly bound agglomerates that can be broken by weak shearing, as applied during the formulation processes. The distribution is relatively monomodal Example 6

Methods

XRPD

XRPD was performed on a PHILIPS PANalytical, X'Pert Pro. diffractometer

The experimental conditions are the following:
Configuration Bragg-Brentano: θ–θ
Source: Cu with Kα1 at λ=1.5406 Å.
The power supply works at 45 kV and 40 mA.
Detector: PSD X'Celerator in scanning mode
Sample temperature: room temperature
Angular variation: from 2θ=3° to 45°
Step size [° 2θ]: 0.008
Scan step time (in s): 13 39
Duration: 20 min according to the diffraction intensity A few mg of sample were prepared on a silicon plate without any special treatment other than a slight pressure to obtain a flat and homogeneous surface for reproducible and repeatable results.

Thermal Analysis (DSC/TGA/Hot Stage)

An accurate amount of compound (mg scale) is set up in 40 µL Al crucible with perforated lids. The heating rate is 20° C./min in a nitrogen gas flow. The heating ranged from 30 to 400° C.

DVS

The temperature and RH are pre-set according to the initial temperature and RH.

Method at 37° C.:
Equilibrating 20 min at 50%
Set from 50% to 0%
Equilibrating 20 min at 0% RH
Set from 0% to 100% by step of 10% RH (50% RH per hour)
3 hours at 100% RH
From 100% RH to 0% RH by step of 10% RH (−50% RH per hour)
Equilibrating 20 min at 0% RH
Set from 0% to 50%
Equilibrating 20 min at 50% RH Particle Size Distribution (Malvern)

A total of 3 measurements by batch were made to ensure repeatable and reproducible results.
Dispersant: Silicon oil. A good dispersion is observed in this media and Compound (1) is not soluble in silicon oil.
Stirring: 2000 rpm
lens: 300RF
Analysis model: polydisperse Presentation code: 3OAE
Number of measurement sweeps: 5000
Density: 1.000 g·cm$^3$
With or without stage of ultrasound Example 7

The overall yield for the production of anhydrous Form I was satisfactory (70% overall) and the material of high purity (99.6%, measured by HPLC). The purity can be determined by the HPLC method described in Example 2, Section I.

A modified crystallization process was successfully implemented to recover approx. 75% yield of anhydrous Form XVI of Compound (1) with satisfactory purity (99.6%, HPLC).

Example 8

Alternate Preparation of Form XVI of Compound (1)

Figure 14A:
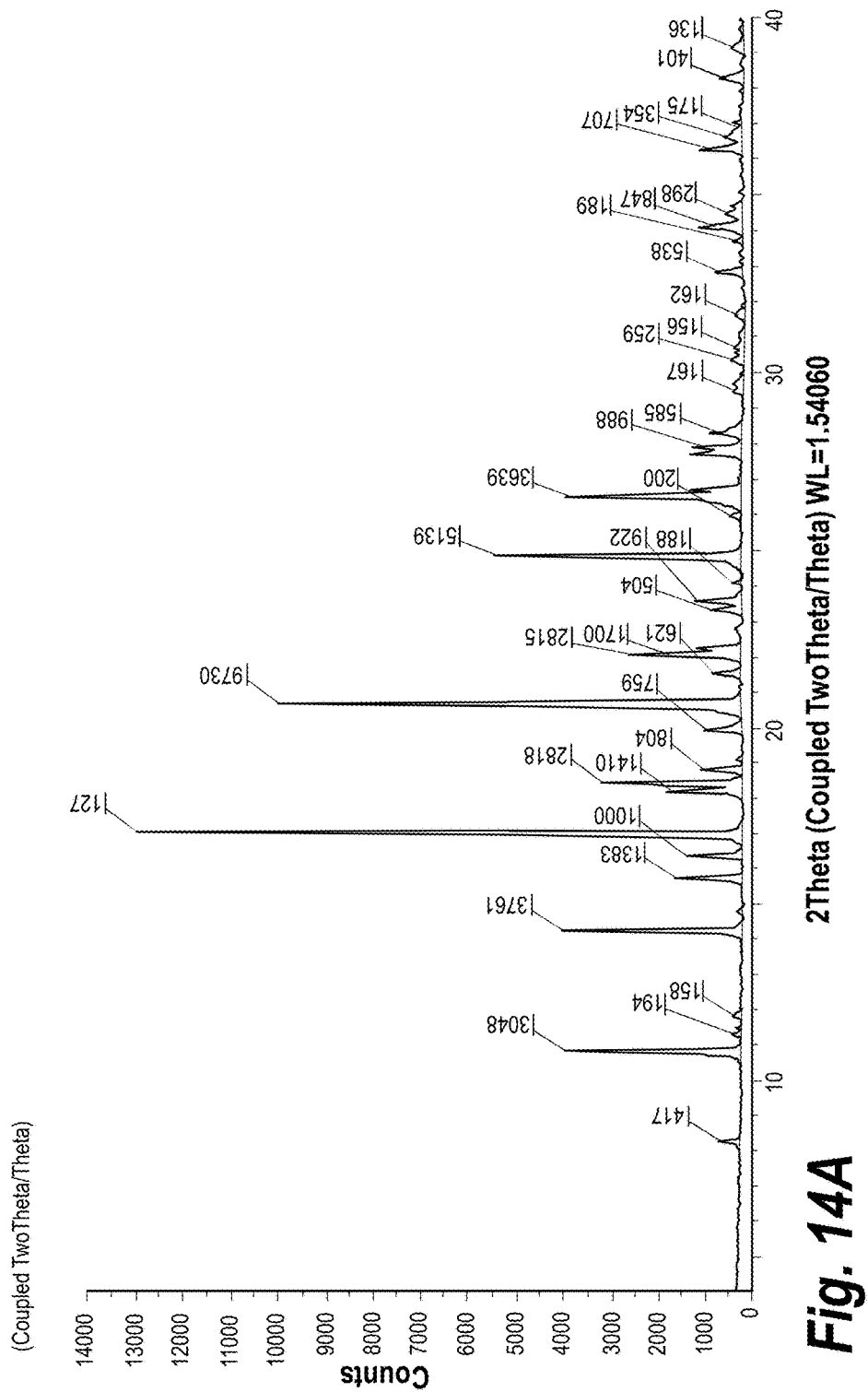
FIG. 14A shows the X-ray powder diffraction pattern of Form XVI of the compound of Formula (1) obtained from the first batch prepared in accordance with Example 8.
Figure 15A:
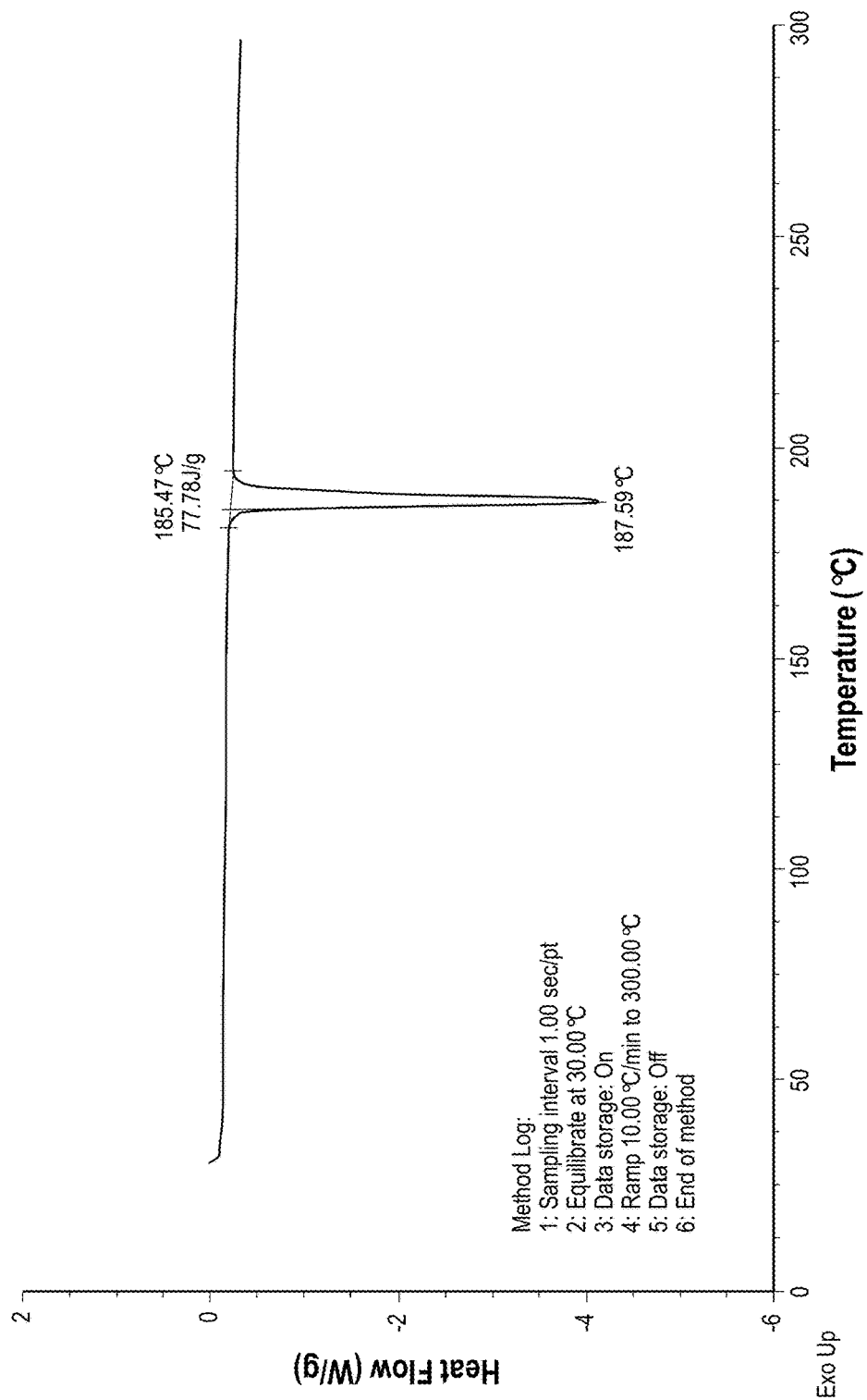
FIG. 15A shows the differential scanning calorimetry (DSC) curve of Form XVI of the compound of Formula (1) obtained from the first batch prepared in accordance with Example 8.

To a 55° C. solution of crude Compound (1) (84.8 kg, 196 mol) in isopropyl alcohol (614 kg) was added seed crystal (Form XVI) of Compound (1) (0.434 kg) and the solution was stirred for 3.5 hours. To this solution was added n-heptane (1,425 kg) and the stirring continued at 55° C. for an additional 2 hours. The temperature of the solution was reduced to 40° C., and stirred at this temperature for another 9 hours. The solid was filtered and the resultant dry cake was oven dried (30° C. for 6 h, and 48° C. for 24 h) to yield 68.7 kg of Form XVI of Compound (1) (81.0% yield, HPLC purity 99.98%, XRPD: FIG. 14A, (XRPD obtained using Cu as the Tube Material, at wave-length alpha 1 of 1.5406 [Å]); DSC: FIG. 15A).

Figure 14B:
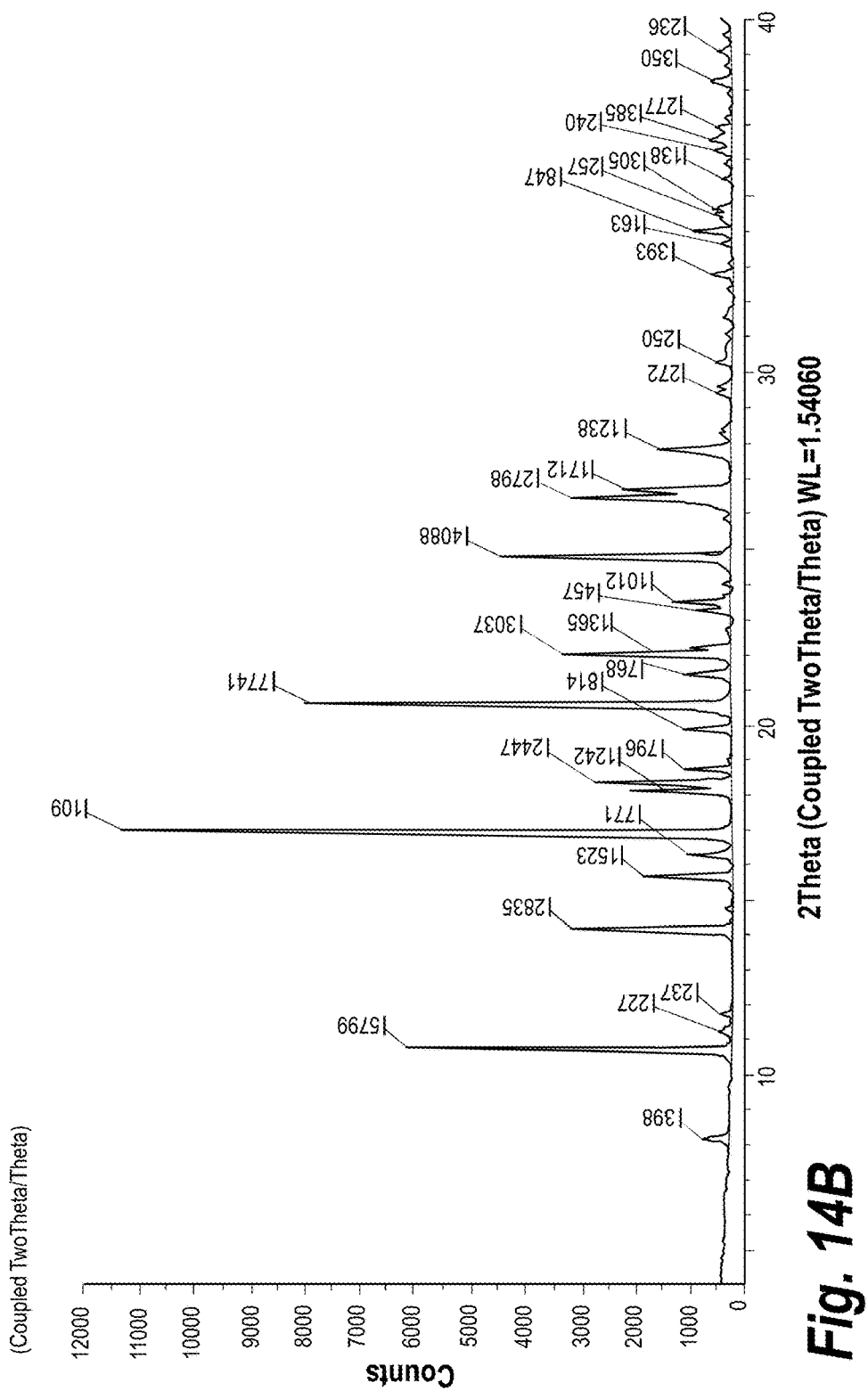
FIG. 14B shows the X-ray powder diffraction pattern of Form XVI of the compound of Formula (1) obtained from the second batch prepared in accordance with Example 8.
Figure 15B:
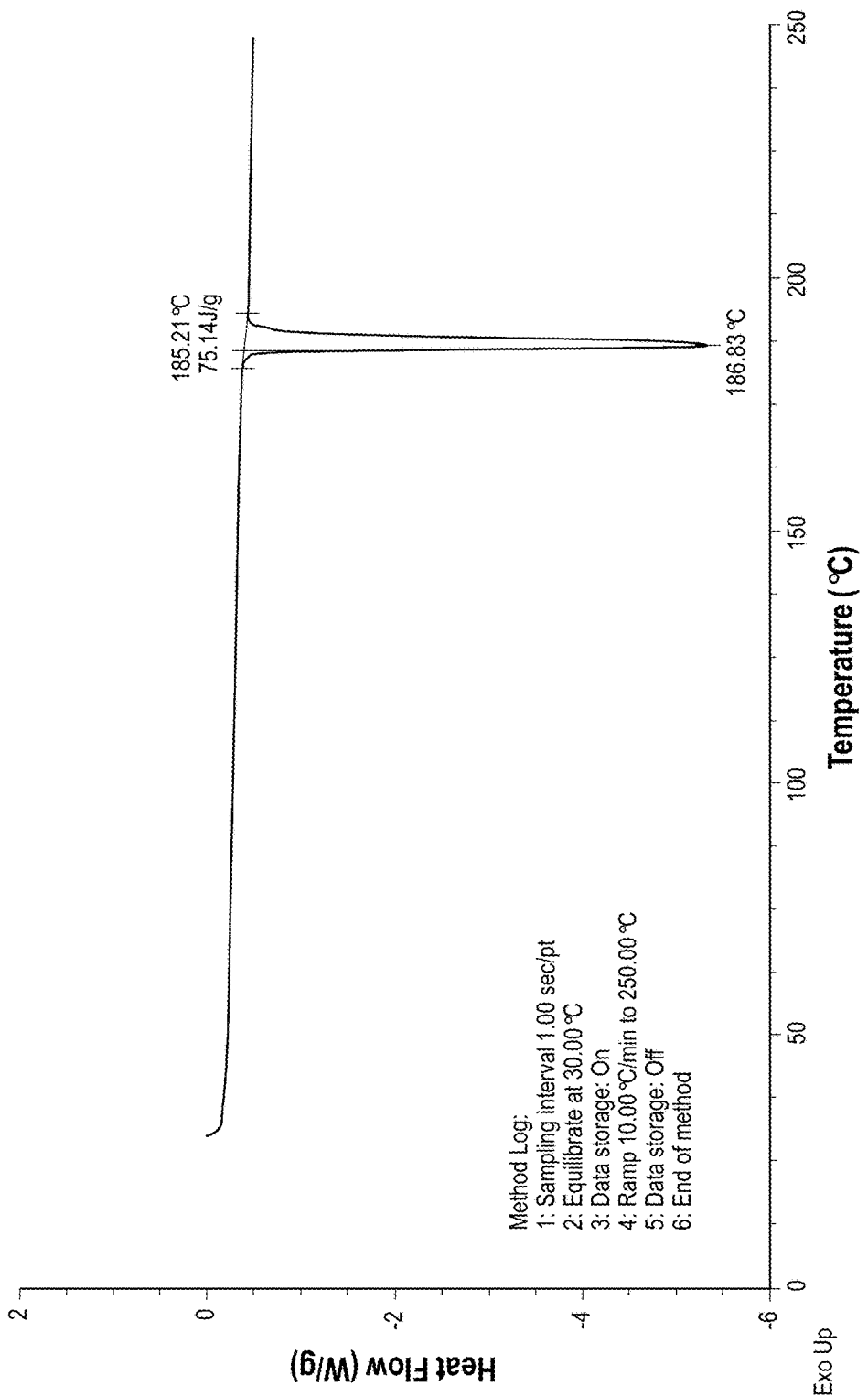
FIG. 15B shows the differential scanning calorimetry (DSC) curve of Form XVI of the compound of Formula (1) obtained from the second batch prepared in accordance with Example 8.

Using the above method, a second batch of crystalline Compound (1) was obtained from 85.1 kg of crude Compound (1) (89.8 kg, 105.5% yield, HPLC purity 99.98%, XRPD (XRPD obtained using Cu as the Tube Material, at wave-length alpha 1 of 1.5406 [Å]): FIG. 14B, DSC: FIG. 15B). The yield of 105.5% was due to residual Compound (1) from the first batch. A combined yield of 93.3% was obtained for both batches.

The invention claimed is:

1. A crystalline form of the compound of Formula (1)

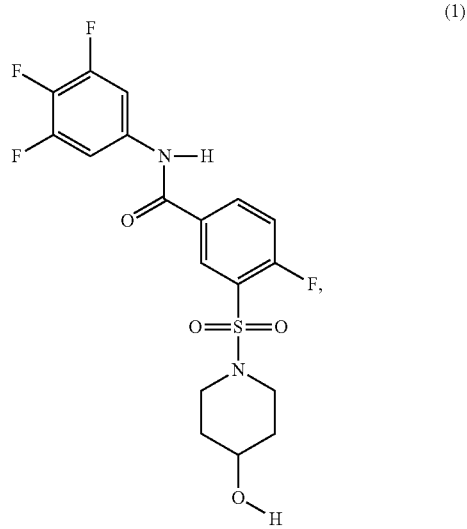 [SMILES: O=C(Nc1cc(F)c(F)c(F)c1)c1ccc(F)c(S(=O)(=O)N2CCC(O)CC2)c1]

(1)

wherein the form is characterized by an X-ray powder diffraction pattern having peaks expressed in degrees-2-theta at angles (±0.2°) of 17.1, 20.8, 22.2, 24.9, and 26.6 (Form XVI).

2. The crystalline form of claim 1, wherein the crystalline form is characterized by a melting point at about 185° C.

3. The crystalline form of claim 1, wherein the crystalline form is characterized by a melting point at about 185±2° C.

4. A pharmaceutical composition comprising a crystalline form of the compound of Formula (1)

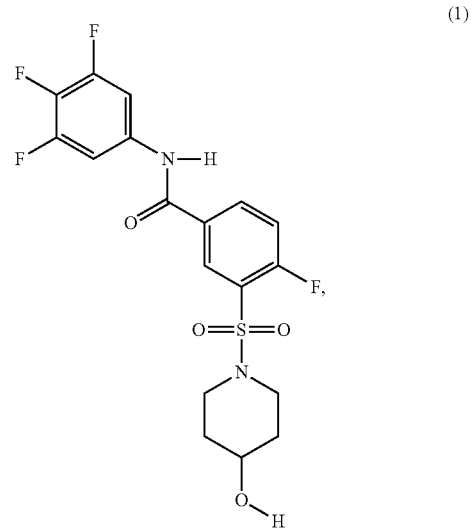 [SMILES: O=C(Nc1cc(F)c(F)c(F)c1)c1ccc(F)c(S(=O)(=O)N2CCC(O)CC2)c1]

(1)

and a pharmaceutically acceptable carrier, wherein the form is characterized by an X-ray powder diffraction pattern having peaks expressed in degrees-2-theta at angles (±0.2°) of 17.1, 20.8, 22.2, 24.9, and 26.6 (Form XVI).

5. A method of treating an HBV infection in a subject in need thereof, comprising administering to the subject a therapeutically effective amount of the crystalline form of the compound of Formula (1)

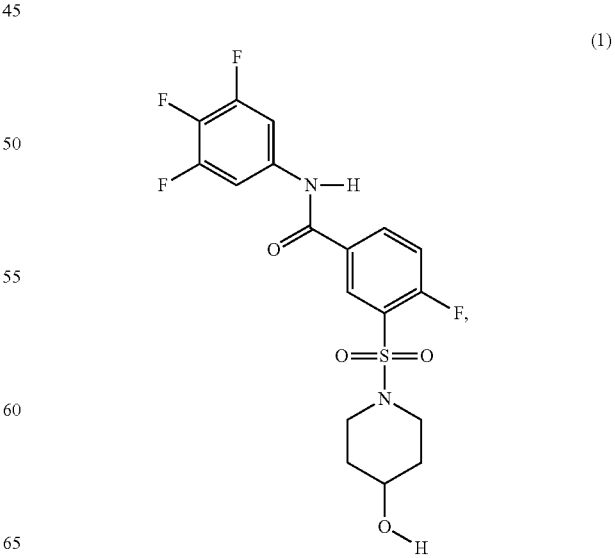

(1)

wherein the crystalline form is characterized by an X-ray powder diffraction pattern having peaks expressed in degrees-2-theta at angles (±0.2°) of 17.1, 20.8, 22.2, 24.9, and 26.6 (Form XVI).

6. A crystalline form of the compound of Formula (1)

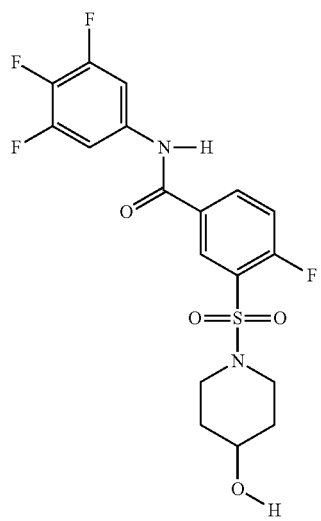

(1)

wherein the crystalline form is characterized by an X-ray powder diffraction pattern having peaks expressed in degrees-2-theta at angles (±0.2°) of 17.1, 20.8, 22.2, 24.9, and 26.6
formed by a process comprising:
(a) adding methyl tert-butyl ether (MTBE) to Compound (1) to form a slurry;
(b) stirring the slurry between about 20° C. and about 30° C.;
(c) filtering the slurry; and
(d) drying between about 50° C. and about 70° C.

7. The crystalline form of claim 6, wherein the crystalline form of the compound of Formula (1) is greater than 90% pure.

8. The crystalline form of claim 6, wherein the crystalline form of the compound of Formula (1) is greater than 95% pure.

9. The crystalline form of claim 6, wherein the crystalline form of the compound of Formula (1) is greater than 99% pure.

10. A crystalline form of the compound of Formula (1)

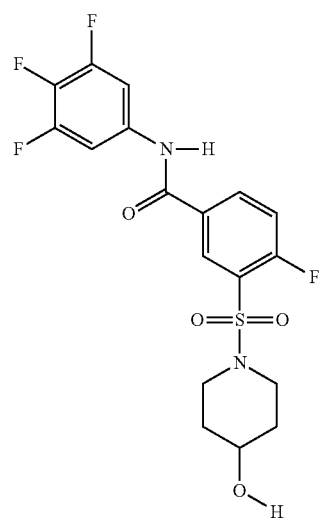

(1)

wherein the crystalline form is characterized by an X-ray powder diffraction pattern comprising peaks expressed in degrees-2-theta at angles (±0.2°) of 17.1, 22.2, 24.9, and 26.6.

11. The crystalline form of claim 10, wherein the crystalline form is characterized by a melting point at 185±2° C.

* * * * *